US011248995B2

(12) United States Patent
Albrecht et al.

(10) Patent No.: US 11,248,995 B2
(45) Date of Patent: Feb. 15, 2022

(54) HYDROGEL ENCAPSULATION OF LIVING ORGANISMS FOR LONG-TERM MICROSCOPY

(71) Applicant: Worcester Polytechnic Institute, Worcester, MA (US)

(72) Inventors: Dirk Albrecht, Worcester, MA (US); Ross Lagoy, Worcester, MA (US); Kyra Burnett, Worcester, MA (US)

(73) Assignee: Worcester Polytechnic Institute, Worcester, MA (US)

( * ) Notice: Subject to any disclaimer, the term of this patent is extended or adjusted under 35 U.S.C. 154(b) by 210 days.

(21) Appl. No.: 16/129,581

(22) Filed: Sep. 12, 2018

(65) Prior Publication Data
US 2019/0078985 A1 Mar. 14, 2019

Related U.S. Application Data

(60) Provisional application No. 62/557,434, filed on Sep. 12, 2017.

(51) Int. Cl.
| | |
|---|---|
| *G01N 1/30* | (2006.01) |
| *G01N 1/44* | (2006.01) |
| *G01N 1/36* | (2006.01) |
| *G01N 21/64* | (2006.01) |
| *G01N 33/483* | (2006.01) |

(52) U.S. Cl.
CPC ............ *G01N 1/30* (2013.01); *G01N 1/36* (2013.01); *G01N 1/44* (2013.01); *G01N 21/6458* (2013.01); *G01N 21/6486* (2013.01); *G01N 33/4833* (2013.01); *G01N 2001/305* (2013.01)

(58) Field of Classification Search
CPC .......... G01N 1/30; G01N 33/4833; G01N 2001/305; G01N 1/36; G01N 1/44; G01N 21/6458; G01N 21/6486
See application file for complete search history.

(56) References Cited

U.S. PATENT DOCUMENTS

| | | | | |
|---|---|---|---|---|
| 4,615,883 A | * | 10/1986 | Nelsen | ............ A01N 63/00 |
| | | | | 119/6.7 |
| 9,399,068 B2 | * | 7/2016 | Heilshorn | ............ A61K 9/0024 |
| 2012/0225101 A1 | | 9/2012 | Kao et al. | |
| 2013/0218143 A1 | | 8/2013 | Ross et al. | |
| 2015/0082465 A1 | * | 3/2015 | Kato | ............ A61K 49/0008 |
| | | | | 800/3 |
| 2015/0290329 A1 | | 10/2015 | Heilshorn et al. | |

FOREIGN PATENT DOCUMENTS

WO 2017031249 A1 2/2017

OTHER PUBLICATIONS

ZEISS White Sheet, Light Sheet Fluorescence Microscopy, Sep. 2013, cited on IDS Nov. 28, 2018 (Year: 2013).*
Torgersen et al., J. Biomedic. Op., 17(10):1-10 (2012) (Year: 2012).*
Gilleland et al., Genetics, 201: 39-46 (2015) (Year: 2015).*
Rohde et al., Genetics, 201: 39-46 (2015) (Year: 2015).*
Yu et al., eNeuro., 4(2):1-16 (2017) (Year: 2017).*
Aubry et al., Lab Chip, 15:1424-1431 (2015) (Year: 2015).*
Bakhtina et al., RSC Adv., 4:4691-4709 (2014) (Year: 2014).*
Bringmann et al., J. Neurosci. Meth., 201:78-88 (2011) (Year: 2011).*
Ciuciu et al., RSC Adv., 4:45504-45516 (2014) (Year: 2014).*
Torgersen et al., Adv. Funct. Mater., 23:4542-4554 (2013) (Year: 2013).*
Flood, et al., "ZEISS Lightsheet Z.1 Sample Preparation", White Paper, Sep. 2013.
International Search Report in International Patent Application No. PCT/US2018/050741 dated Nov. 9, 2018.

* cited by examiner

*Primary Examiner* — Kade Ariani
(74) *Attorney, Agent, or Firm* — Greenberg Traurig, LLP; Roman Fayerberg

(57) ABSTRACT

Devices and methods for capturing and imaging a specimen, such as a living organism, are disclosed. In some embodiments, a method for imaging a living organism in vivo includes placing at least one specimen into a hydrogel polymer on a substrate, and curing the hydrogel to embed the at least one specimen within the cured hydrogel such that the at least one specimen is kept alive and the movement of the at least one specimen within the cured hydrogel is restricted. The at least one embedded specimen can be imaged.

19 Claims, 41 Drawing Sheets

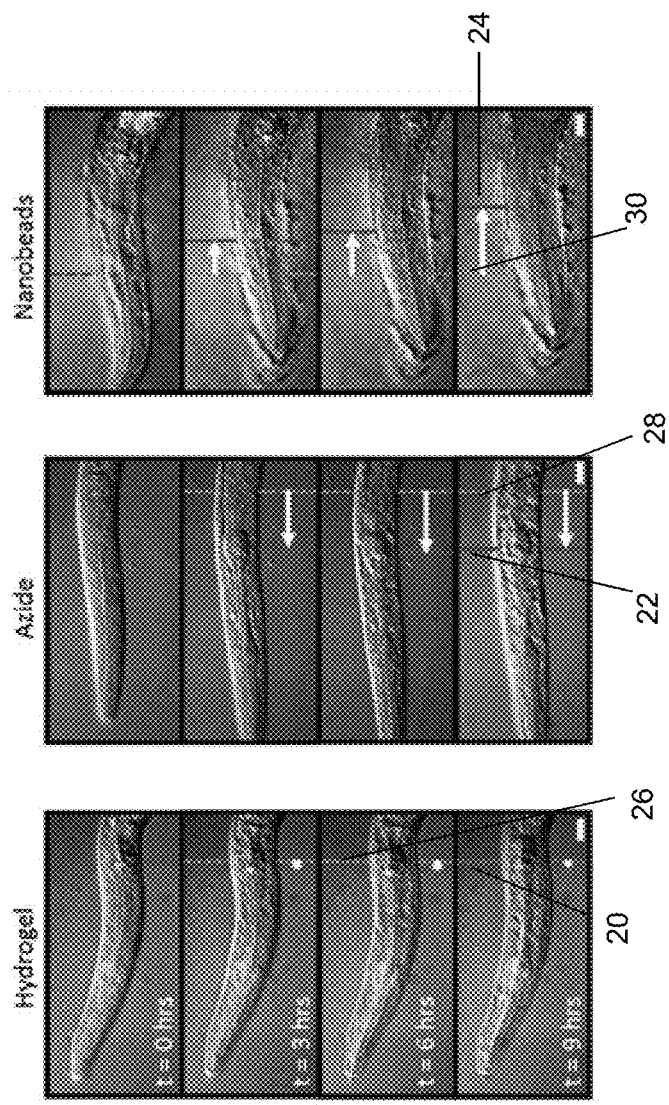

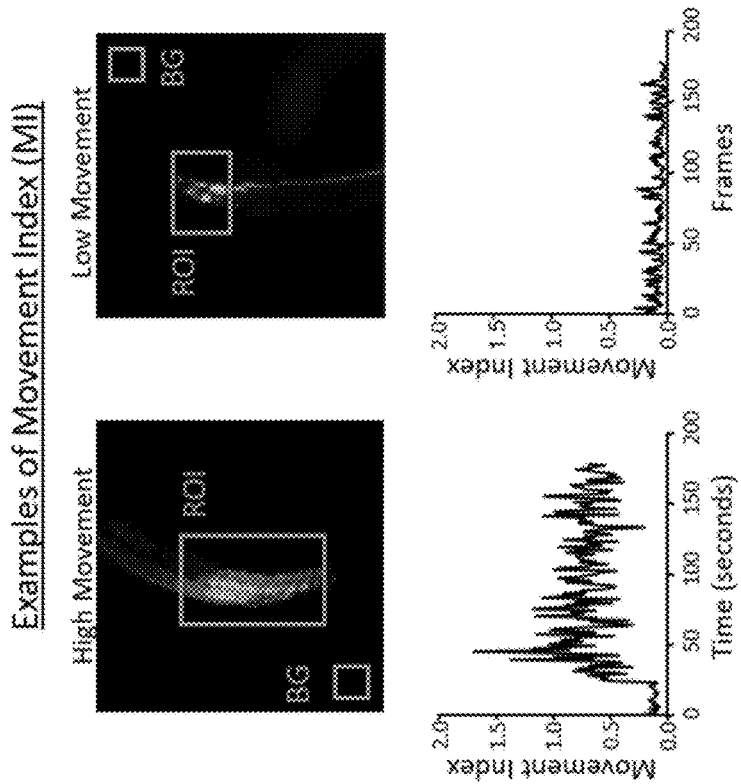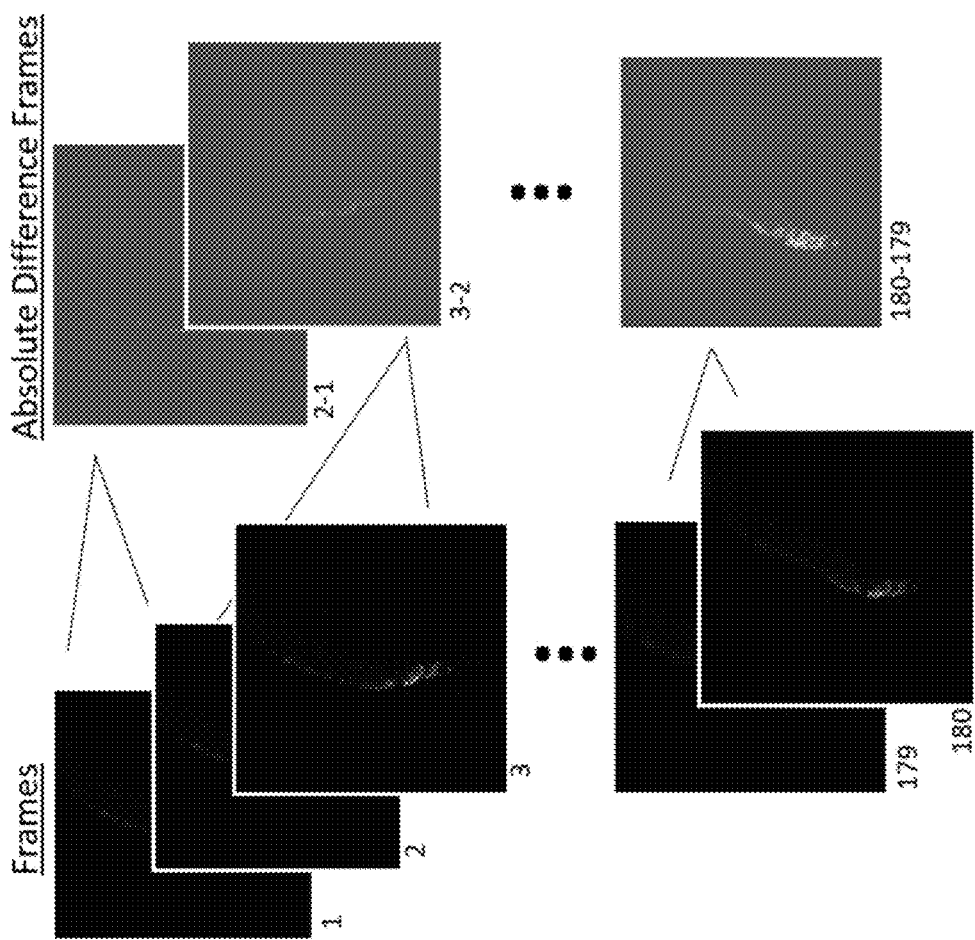
FIG. 5

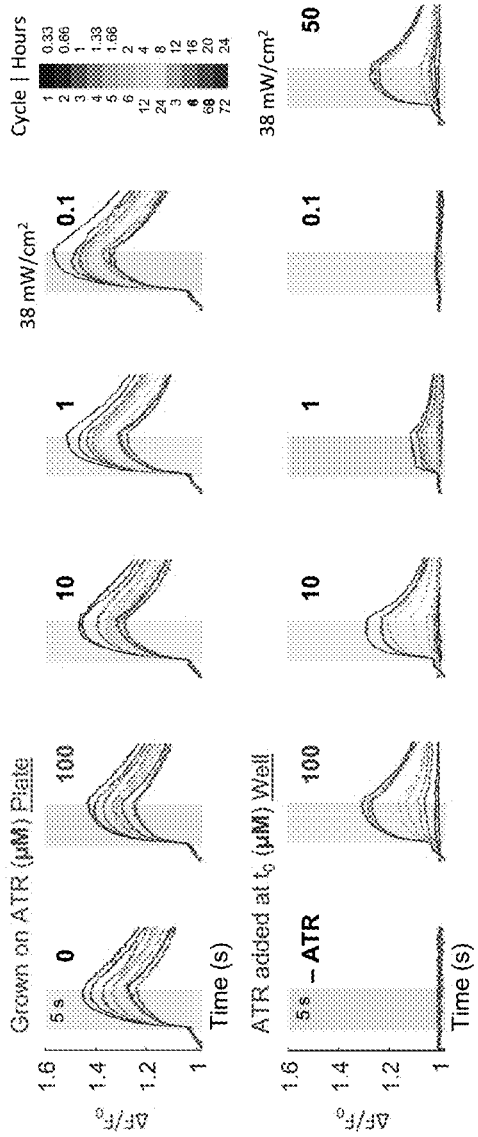
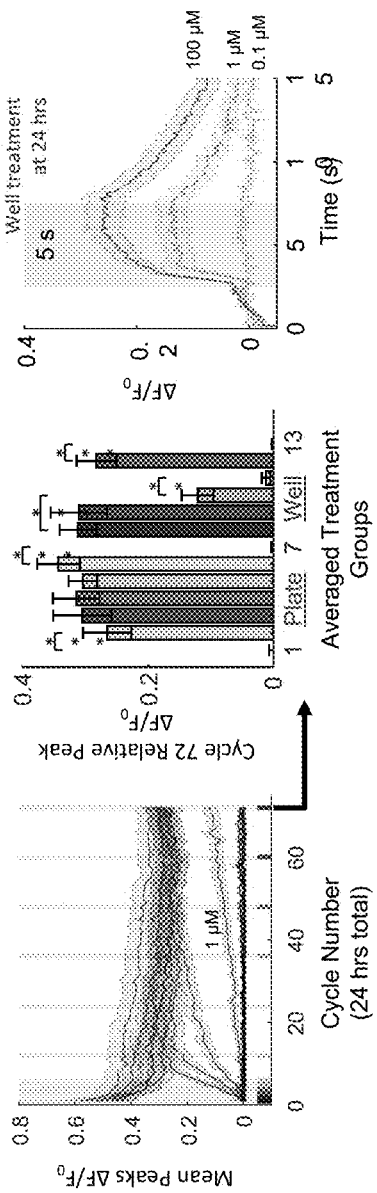
FIG. 13C
FIG. 13D
FIG. 13E
FIG. 13F
FIG. 13G

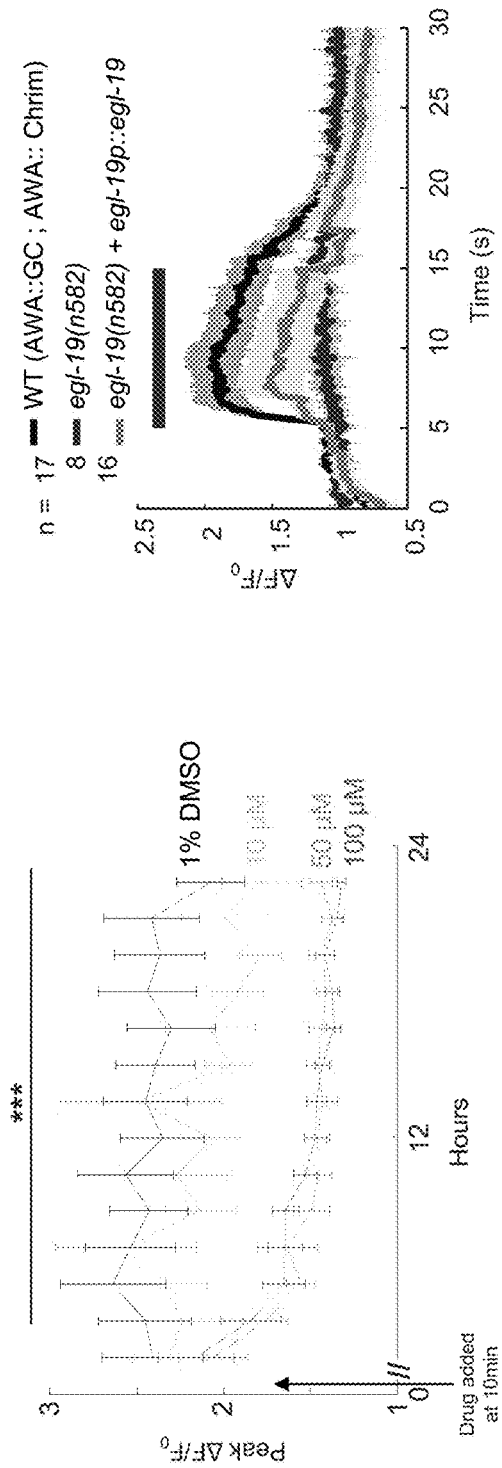
FIG. 14C
FIG. 14D
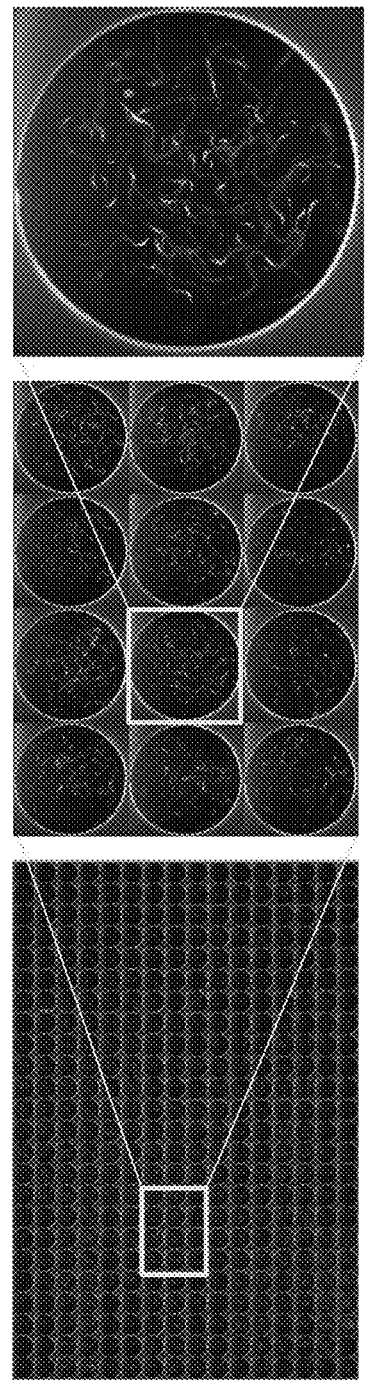
FIG. 14E

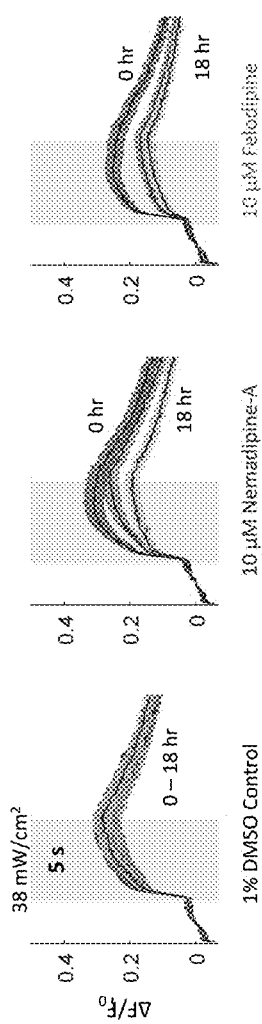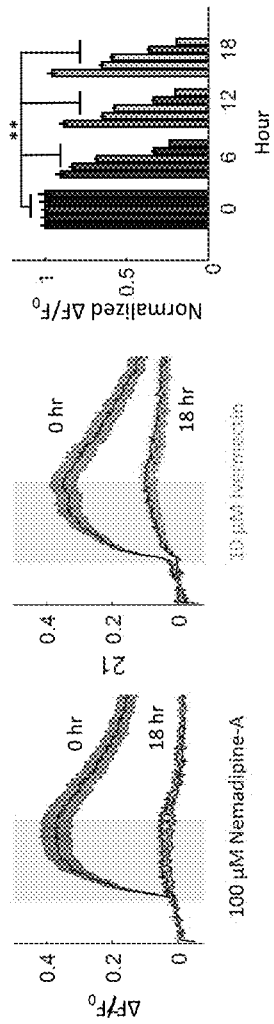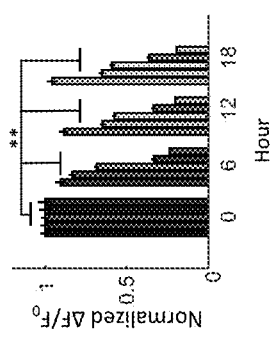

Gel puck placed onto agar plate

Gel puck removed from well

Gelled animals in 1 well

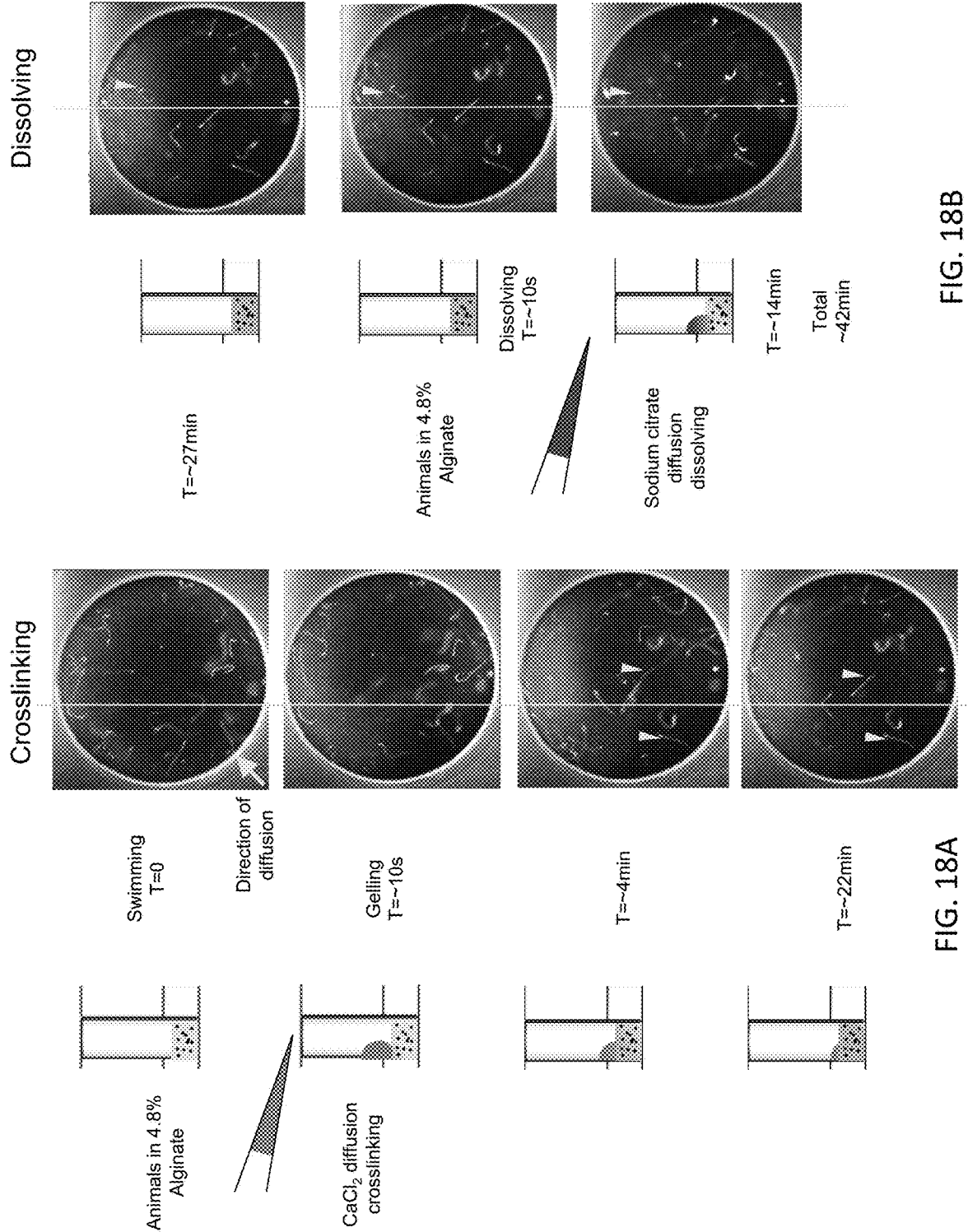

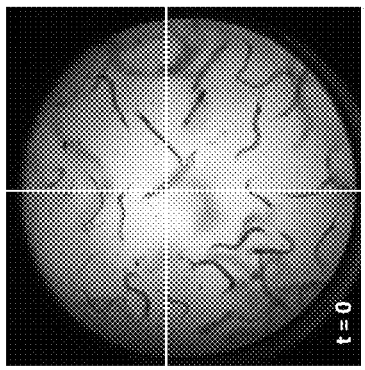
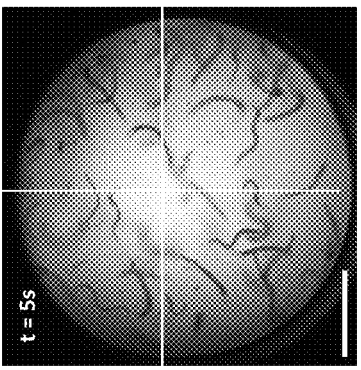
FIG. 19A
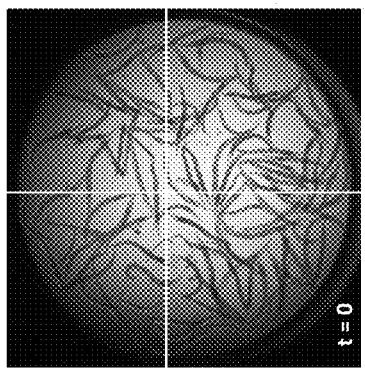
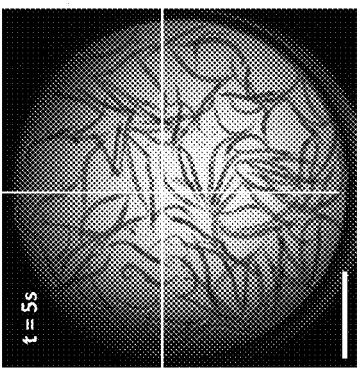
FIG. 19B
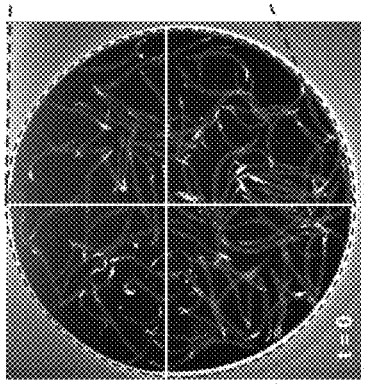
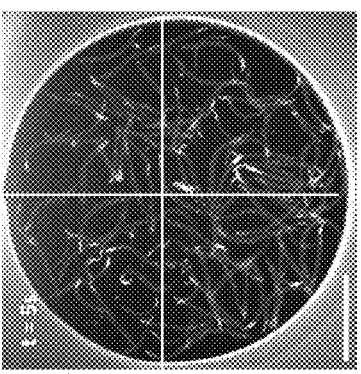
FIG. 19C
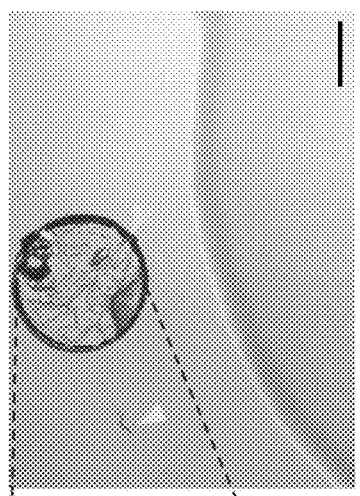
FIG. 19D
FIG. 19E

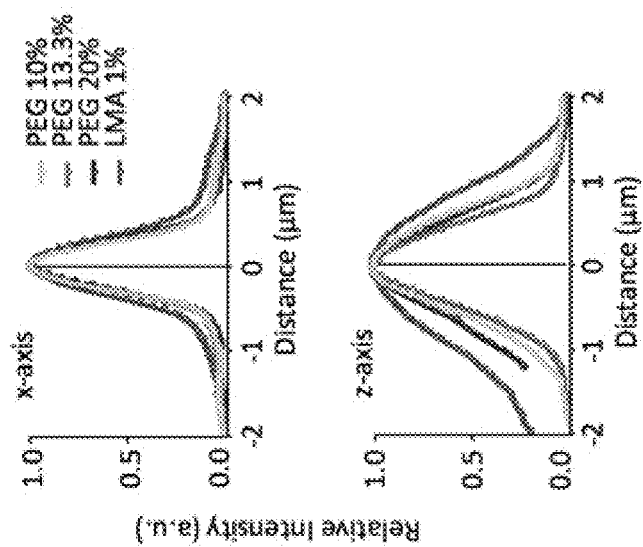
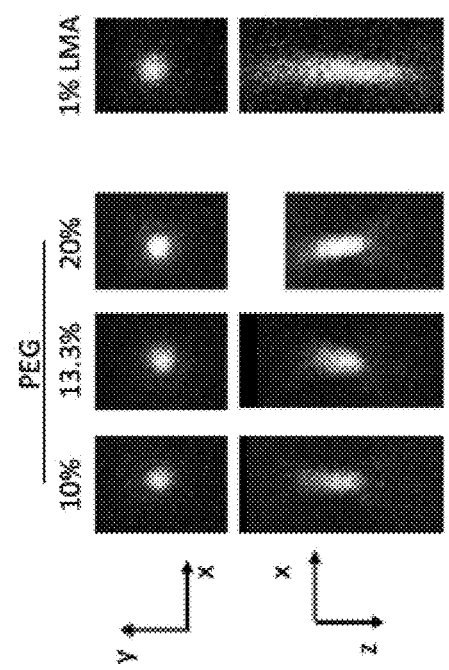
FIG. 23A
FIG. 23B

HYDROGEL ENCAPSULATION OF LIVING ORGANISMS FOR LONG-TERM MICROSCOPY

RELATED APPLICATIONS

This application claims the benefit of and priority to U.S. Provisional Application Ser. No. 62/557,434, filed Sep. 12, 2017, which is incorporated herein by reference in its entirety.

STATEMENT OF GOVERNMENT SUPPORT

This invention was made with Government Support under Grant Number CBET 1605679 awarded by the National Science Foundation. The Government has certain rights in the invention.

FIELD

The disclosure relates generally to compositions, methods, and devices for immobilization of organisms for in vivo studies.

BACKGROUND

Small model organisms are widely used for in vivo studies of basic physiology and systemic responses. Many imaging techniques require reliable immobilization of the sample during imaging periods while simultaneously preserving the organism's health and maintaining the function of fluorescent markers for the duration of the experiment. In addition to addressing sample conditions such as hydration, temperature, and nutritional environment, imaging parameters such as light exposure intensity must be carefully optimized for maximal signal with minimal phototoxicity and sample perturbation.

Current immobilization methods suffer from a number of shortcomings, such as, use of toxic reagents and inability to support health of the organisms for the duration of the studies. Accordingly, there is still a need for materials and methods that provide a rapid, gentle, versatile, and inexpensive alternative mounting method useful for continuous long-term imaging.

SUMMARY

In some aspects, a method for imaging a living organism in vivo is provided, that includes placing at least one specimen into a hydrogel polymer on a substrate, and curing the hydrogel to embed the at least one specimen within the cured hydrogel such that the at least one specimen is kept alive and the movement of the at least one specimen within the cured hydrogel is restricted. The at least one embedded specimen is imaged.

In some embodiments, the at least one specimen comprises one or more cells. In some embodiments, the at least one specimen comprises one or more whole organisms. In some embodiments, the at least one specimen is kept alive for at least 24 hours. In some embodiments, the at least one specimen is mounted using glass slide mounting. In some embodiments, the method further includes releasing the at least one specimen from the cured hydrogel such that the as least one specimen remains alive.

In some embodiments, the method further includes delivering a stimulus to the at least one specimen and imaging a response of the at least one specimen to the stimulus. In some embodiments, imaging the at least one specimen includes image acquisition-based screening for detection of change in at least one of one or more fluorescent signals, movement of the at least one specimen, or quantities over time. In some embodiments, the method further includes analysing the effect of one or more compounds introduced into the cured hydrogel on acquired signals related to the at least one specimen.

In some embodiments, the imaging of the at least one specimen is done with light sheet microscopy. For example, the at least one specimen can be mounted using standard capillary mounting.

In some aspects, a method for immobilizing samples in a multi-well plate is provided, and includes mixing a curable hydrogel solution with a population of specimens, and distributing the mixture of the hydrogel solution and the specimens among a plurality of wells of a multi-well plate. The hydrogel solution is cured in each well to embed the specimens in the hydrogel in a confined space, movement of the specimens being restricted to the confined space. The specimens are maintained in a living state for a threshold amount of time.

In some embodiments, the specimens comprise one or more cells. In some embodiments, the specimens comprise one or more whole organisms. In some embodiments, the method further includes settling the specimens on a bottom of the wells prior to the curing the hydrogel. In some embodiments, the method further includes synchronizing the specimens prior to the mixing the specimens and the hydrogel solution. In some embodiments, the threshold for maintaining the specimens in the living state is at least 24 hours.

In some embodiments, the method further includes delivering a stimulus to the specimens and imaging a response of the specimens to the stimulus. In some embodiments, the method further includes simultaneously delivering one or more stimuli to the specimens in different wells and imaging the specimens.

In some aspects, the present disclosure provides a sample for tests that includes a cured hydrogel having a confined space defined within the hydrogel, and one or more living specimens inside the confined space. Movement of the specimens is restricted to the confined space, and the specimens are maintained in a living state for a threshold amount of time.

In some embodiments, the specimens comprise one or more cells. In some embodiments, the specimens comprise one or more whole organisms.

In some aspects, a multi-well plate wherein the sample is distributed among multiple wells of the multi-plate well.

In some aspects, the present disclosure provides a method for preparing an organism for imaging, including providing at least one specimen, and embedding the at least one specimen within a hydrogel in a confined space within the hydrogel. The movement of the at least one specimen is restricted within the confined space and is maintained in a living state.

In some embodiments, a method for preparing an organism for imaging is provided, the method comprises the steps of providing an organism and embedding the organism within a hydrogel to create a confined space within the hydrogel, whereby movement of the organism is restricted within the confined space.

In some embodiments, a method for imaging an organism in vivo with light sheet fluorescence microscopy (LSFM) is provided, the method comprises the steps of placing an organism into a hydrogel polymer on a substrate, curing the hydrogel to embed the organism within the cured hydrogel such that the organism is kept alive and the movement of the organism within the cured hydrogel is restricted, and imaging the organisms on the substrate.

BRIEF DESCRIPTION OF THE DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein:

FIGS. 1A-1F show mounting live *C. elegans* in hydrogels and on agarose pads for microscopy and recovery from hydrogels;

FIG. 5 shows movement index calculations used in the analysis of hydrogel-embedded animal movement;

FIGS. 13A-13G shows an automated assessment of a 24-hour time course and ATR dose response threshold for optogenetically-evoked calcium responses in *C. elegans*;

FIGS. 14A-14D shows how the calcium channel blocker Nemadipine-A has time and dose dependent effects on AWA activity in wild-type and egl-19 calcium channel mutants;

FIG. 14E shows well-plating according to an application of the process disclosed herein;

FIGS. 15A-15K show an exemplary embodiment of the identification of optogentically-evoked calcium activity suppressors using the automated long-term high-content functional screening method;

FIG. 18A and FIG. 18B show immobilization of animals in a multi-well plate with alginate ionic crosslinking and subsequent dissolution for recovery from the well-plate;

FIGS. 19A-19E illustrate an exemplary embodiment of an immobilization of an organism in one well of a 384 well plate using the hydrogel, and successful recovery of embedded animals;

FIGS. 23A-23E compare the optical resolution and autofluorescence of different concentration PEG hydrogels and low-melt agarose.

Figure 1A:
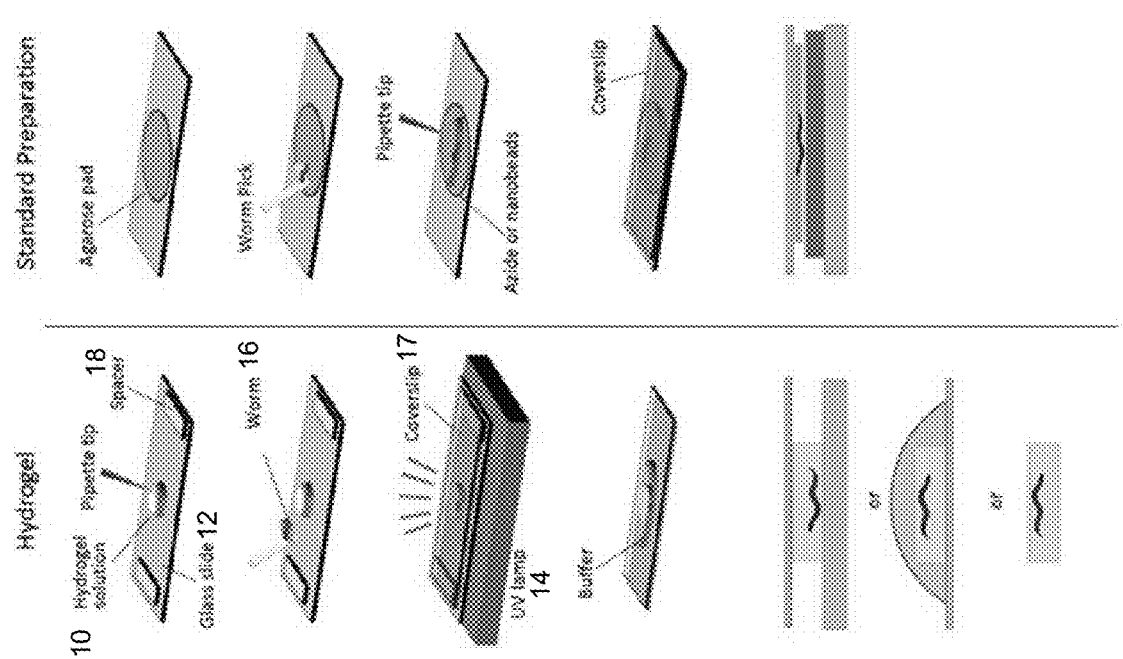

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

In some embodiments, there is provided a process for encapsulating living organisms in a hydrogel environment that enables rapid and gentle immobilization for long periods of time. Chemical compositions and physical constraints can provide hydrogel encapsulation of living organisms for use in various applications that require different geometries, including but not limited to long-term light-based wide-field imaging (for example, bright-field and fluorescence), high-resolution three-dimensional microscopy (for example, confocal and light sheet), and high-content in vivo functional screening of organisms immobilized in multiwell plates. The encapsulation process can use standard lab equipment and readily available materials, work with any size organism, including all larval and adult stages, and can be performed at any desired temperature. The organism is placed into a polymer droplet prior to crosslinking, which locks the organism in place.

In some embodiments, the hydrogel material can be in the form of a mixture of three components (polymer, crosslinker, and solvent such as an aqueous buffer). A light source, such as a UV light source, can be used to cause for inducing phase changes of the mixture from a liquid to gel (within seconds) due to the chosen photo-crosslinker, wavelength, and intensities. Depending on the application, the hydrogel can be tuned in all aspects of the composition to meet specific biological requirements, geometric constraints (for example, well plates, glass capillaries, standard glass microscope slides, etc.), or a combination of each. The general steps of the process are: (1) prepare solutions and materials, (2) transfer living organisms (after pre-treatment, if desired) to the hydrogel polymer liquid, (3) crosslink the hydrogel, encapsulating organisms, (4) transfer the hydrogel and organisms to the desired buffer and test instruments.

As explained above, in some embodiments, the composition of the hydrogel material includes three components for successful polymerization: (1) the polymer (for example, PEGDA powder), (2) crosslinker (for example, Irgacure powder), and (3) solvent (for example, water). In reference to FIGS. 1A-1F, in some embodiments, one or more living organisms can be encapsulated (e.g., immobilized for study) in a covalently-crosslinked hydrogel composition 10. In some embodiments, the polymer composition comprises polyethylene glycol (PEG) having reactive end-groups, for example PEG diacrylate (PEG-DA) and PEG dimethacrylate (PEG-DMA). In other embodiments, the hydrogel composition can comprise copolymers such as poly(ethylene glycol) (PEG)/silica polymers, PEG-Fibrinogen, PEG-Albumin, PEG-Gelatin polymers, poly(ethylene glycol)-grafted-chitosan (PEG-g-CS) polymers, and polyethylene glycol maleimide (PEG-MAL) polymers.

The hydrogel can be crosslinked, or cured, using a variety of techniques, such as with chemical or physical crosslinking. In some embodiments, the curing technique can be in-part dependent on the desired application, geometry for gelation, and/or compatible organism chemistries and environments. Additionally, the chosen curing process can be dependent of the chosen polymer and solvent. In some embodiments, the hydrogel can be photocrosslinked, or cured, using a photoinitiator. In some embodiments, the photoinitiators are sensitive to UV or visible light. Non-limiting examples of photoinitiators include Irgacure 2959, 2-hydroxy-4-(2-hydroxyethoxy)-2-methylpropiophenone, a UV-sensitive initiator; lithium phenyl-2,4,6-trimethylbenzoylphosphinate (LAP), a blue-light-activated initiator; 2,2-dimethoxy-2-phenyl-acetophenone in 1-vinyl-2-pyrolidinone; 1-hydroxycyclohexyl phenyl ketone (Irgacure 184); 2,2-dimethoxy-2-phenylacetophenone (Irgacure 651); and 2-methyl-1-[4-(methylthio)phenyl]-2-(4-morpholinyl)-1-propanone (Irgacure 907). In some embodiments, the covalently-crosslinked hydrogel immobilizes the organism within seconds of light exposure, and retains it in place permanently for long-term studies, yet can be easily broken to recover the organism. In some embodiments, PEG hydrogels can be crosslinked by a variety of UV-A and UV-B lamps, for DNA gel documentation. Gelation time is dependent on the amount of light absorbed by the photoinitiator: shorter-wave UV-B sources (308, 312 nm) crosslinked faster as they better match the photoinitiator absorbance compared with UV-A sources (365 nm).

In some embodiments, the hydrogel can be chemically crosslinked with oxidizing agents such as ammonium persulfate (APS) and sodium persulfate (NaPS). Direct chemical crosslinking can also be used to form intra- or intermolecular bonds by mixing of compatible oxidizing agents, instead of exposure to ultraviolet light as described above. This is a useful application for immobilizing samples without needing extra equipment for curing (like the UV light source), but there is less control of the crosslinking process.

In some embodiments, the hydrogel can be ionically crosslinked, such as using 1-5% alginate with a divalent cation, such as 100 mM $CaCl_2$). Physical, or ionic, curing is an alternative to radical polymerization, which utilizes a stabilization of charges within electron-releasing and -withdrawing monomers and causes molecular bonding. With this, the hydrogel can be dissolved with a cation chelator, such as sodium citrate for calcium. This technique is useful for restoring the solid gel-phase to a liquid phase by changing the chemical environment. This technique can be compatible in a 384 well plate format to immobilize then restore freely swimming *C. elegans*. The reversibility of this approach is useful for rescuing samples without physically damaging a variety of specimens in various geometries that would otherwise be difficult using chemically crosslinked approaches.

In some embodiments, a process includes immobilizing a living organism by encapsulating it within a hydrogel, thereby gently restricting movement of the organism within the confined spaces. The hydrogel is thereby used as an embedding medium for continuous long-term imaging and/or other studies involving the organism. In some embodiments, the organism is mounted and immobilized such that it is gently encapsulated in a non-toxic, photosensitive PEG hydrogel, and trapped within a small confined volume. PEG hydrogels can be crosslinked in various sizes, making this approach suitable for embedding biological samples from >1 µm to mm or larger, a size range spanning from bacteria, yeast, and mammalian cells to small organisms including but not limited to nematodes, marine organisms (such as squid and jellyfish), *C. elegans, Drosophila*, and zebrafish. Additionally, the solvent compatibility can be tuned to more appropriately resemble the natural environment in which animals are raised or remain healthy, such as oceanic conditions for marine organisms, or isotonic solutions for sensitive hyper- or hypoosmotic physiological states. These conditions can also be tuned irrespective of the natural organism environment to cause desired changes in animal or organism physiology.

The process is versatile, allowing a wide range of hydrogel size, stiffness and diffusivity. The process can also enables tuning the degree of organism constraint.

In some embodiments, the process can allow for a wide range of hydrogel sizes. Hydrogel size is virtually unlimited, ranging from microns to centimetres or more, as it gels uniformly throughout a volume. Hydrogel size and geometry is controlled by the volume deposited and the containment system, such as two parallel glass slides and a spacer to create hydrogel disks. The hydrogel can be shaped by a containment mold which can be micropatterned, as described below.

In some embodiments, the process can allow for a wide range of hydrogel stiffness. For example, the mechanical stiffness and/or chemical properties of the hydrogel (i.e., diffusivity of the hydrogel, relative to surrounding solutions) can be tuned, using various polymer concentrations. Mechanical stiffness ranges from 10 to >1000 kPa with PEG-diacrylate concentrations ranging from 10%-40% (w/v) and chain lengths from 500 Da to 10 kDa. Higher PEG-DA concentrations and shorter chain lengths increase stiffness. For example, mechanical stiffness increases 10-fold from 30 to 300 kPa between 10 and 20% (w/v) concentrations of PEG-diacrylate (PEG-DA, 3 kDa). For manual handling of hydrogels, a range of 15-20% (w/v) can be used. Thus, between 10%-20% (w/v) concentrations of PEG-diacrylate (PEG-DA, 3 kDa), mechanical stiffness increases 10-fold with from 30 to 300 kPa, whereas mesh size decreases from 4 nm to 3 nm over this range, reducing diffusivity. In these hydrogels, small molecules can diffuse freely, but larger proteins cannot. Longer PEG-DA monomer chains can extend pore size over 15 nm, enabling diffusion of small proteins. Bacterial food would not permeate the hydrogel and embedded animals could not be fed by applying a bacterial suspension, although they could be nourished by a chemically defined medium such as *C. elegans* Maintenance Medium (CeMM). In some embodiments, the geometry (i.e., any shape that contains the hydrogel and initiators) can also be tuned.

In some embodiments, the process can allow for a wide range of hydrogel diffusivity. Mesh size, or the average distance between adjacent crosslinks, ranges from 0.5 nm to 16 nm with PEG-diacrylate concentrations ranging from 10%-40% (w/v) and chain lengths from 500 Da to 10 kDa. Thus, hydrogel diffusivity can be tuned to allow free diffusion of small molecules while restricting larger proteins, or to allow diffusion of small proteins as well. For example, mesh size can decrease from 4 to 3 nm between 10 and 20%

(w/v) concentrations of PEG-diacrylate (PEG-DA, 3 kDa). In these hydrogels, small molecules can diffuse freely, but larger proteins cannot. Longer PEG-DA monomer chains can extend pore size over 10 nm, enabling diffusion of small proteins, while still immobilizing animals. Large food particles, such as bacterial food, would not permeate the hydrogel, although embedded animals in principle could be nourished by a chemically defined medium such as *C. elegans* Maintenance Medium.

Diffusion time of molecules (that are smaller than the hydrogel mesh size) ranges from seconds to hours, depending on molecular size and diffusion distance into the hydrogel. Diffusivity in the hydrogel is approximately one-half that of a stationary aqueous fluid (Hagel, V., Haraszti, T. & Boehm, H. Biointerphases (2013) 8: 36). Diffusion time through a hydrogel slab (3D) is $t_d = x^2/(6 k D)$ where k is the ratio of diffusivity in hydrogel vs. in water, D is diffusivity in water, and x is the diffusion distance. Diffusion time of a small molecule ($D = 5 \times 10^{-6}$ cm$^2$/s) through an x=0.1 mm slab is about 7 seconds, and diffusion to an organism embedded x=20 microns beneath the surface is ~0.25 s. Therefore, small molecule concentration can be changed rapidly. In a 384-well plate, organisms may be about 1 mm below the gel surface, giving a diffusion time of small molecule drugs of about 10 min. Proteins ($D = 1 \times 10^{-6}$ cm$^2$/s) diffuse much slower, with a diffusion time of 35 s across 0.1 mm, and about 1 hour across 1 mm.

In some embodiments, the process includes immobilizing organisms such that they maintain a normal morphology, rather than being compressed between impermeable cover slips. In some embodiments, the process includes surrounding the organisms with a permeable hydrogel, such that they may be fully hydrated for prolonged periods of time. In some embodiments, the process includes immobilizing organisms in the hydrogel such that they are recoverable and viable after a period of encapsulation (e.g., 24 hours). For example, *C. elegans* can continue to elicit neural responses after 24 hours of encapsulation, and even days after. High-resolution image quality was maintained over 9 hours of recording *C. elegans* embedded in in PEG hydrogels (FIG. 1). *C. elegans* are also physically recoverable after 24 hours by breaking the hydrogel, allowing for animals to escape and propagate with viable progeny. Organisms can be able to survive encapsulated for longer, and also offer the opportunity to observe nutrient limitations using reporter strains or changes in morphology and/or physical features. The upper limits to encapsulation time depend on the organism's requirements for nourishment, physical movement, and physical expulsion of material. Chemically-defined liquid media may be needed to penetrate the hydrogel network. Some organisms require physical movement for proper development or health after several days. Others must expel materials, such as eggs in *C. elegans*. For example, after about 30 hours, eggs within unfed gravid adult animals may hatch within the body, consuming the body and killing the adult. While eggs can be laid in hydrogel cavities, starvation inhibits egg-laying; this can be reversed chemically, such as by addition of serotonin or certain food odors. Dauer-stage *C. elegans*, which have no feeding requirements, can survive in the hydrogel for months. Single-celled organisms (bacteria, yeast, etc) and mammalian and plant cells can survive encapsulated in the hydrogel for many weeks. In some embodiments, the organisms can be encapsulated for up to 30 hours. In some embodiments, the organism can be encapsulated for between 1 and 4 weeks.

In some embodiments, the hydrogel encapsulation is used in conjunction with light imaging and microscopy techniques including but not limited to wide-field (bright field and fluorescence), phase-contrast, Hoffmann Modulation contrast, and differential interference contrast (DIC) microscopy, such as for identification of cellular features (for live animal laser surgeries) and microinjections. In some embodiments, hydrogel encapsulation is used to immobilize living or nonliving samples for three-dimensional microscopic imaging. Some examples include laser scanning confocal microscopy and spinning disk confocal microscopy. These techniques exclude out-of-plane fluorescence emission. Individual 2-D slices can be combined into a 3-D volumetric image. In some embodiments, the hydrogel is used to immobilize living cells or organisms for advanced 2-D and 3-D imaging techniques, including but not limited to polarization microscopy, multispectral microscopy, structured illumination microscopy, and super-resolution microscopy. In addition to light microscopy, hydrogel encapsulation can be used with atomic force microscopy, such as for live imaging of immobilized samples with corresponding force measurements. Due to the versatility and ease of encapsulation, this technique may also be useful in low-resource settings and with economical microscopy alternatives, like Foldscope.

In some embodiments, the hydrogel encapsulation is used in conjunction with light sheet fluorescence microscopy (LSFM), a modality for continuous long-term 3D imaging that reduces photobleaching by more than an order of magnitude compared with confocal systems. LSFM requires that both the excitation light and the emitted fluorescence pass through refractive index-matched materials, complicating its use with standard mounting methods. Most LSFM protocols embed organisms in low melting point agarose, but image quality is reduced by animal movement, light scattering, and autofluorescence. By physically preventing thrashing in organisms (e.g., larval and adult worms), the hydrogel encapsulation method facilitates the study of post-embryonic processes in a light sheet system, and 3D neural imaging method compatible with long-term optogenetic stimulation.

In the standard LSFM sample mounting process, low melt agarose is melted and brought to 37° C., then the sample (e.g. organism) is added to the agarose. The sample is drawn into a glass capillary and the agarose is allowed to cool, then, the agarose cylinder is partially pushed out until the sample is outside the capillary. PEG-DA hydrogels can be used with commercial light-sheet systems that use the capillary sample mounting method (FIG. 20). Whereas living nematodes encapsulated in low melt agarose per standard protocol move substantially, distorting the 3D reconstructed images, PEG hydrogel can keep them still for high resolution volumetric images over long periods of time.

In reference to FIG. 1A, in some embodiments, to prepare a photocrosslinked hydrogel to mount a LSFM sample, the sample is placed into a drop of hydrogel polymer 10 on a slide 12 with photoinitiator and drawn into a capillary. The hydrogel 10 is crosslinked by exposure to UV light 14, and then the hydrogel cylinder is partially pushed out until the sample is outside the capillary. Other light sheet systems, such as diSPIM, use a standard flat glass substrate as a base. For these systems, the sample is placed into a hydrogel droplet on a hydrophobic glass slide and covered with a methacrylate-silane-treated coverslip. Spacers determine the thickness of the hydrogel disk. For example, spacer dimensions can range from 100-500 μm, but can allow for gelling to a cubic centimeter or larger volume such as curing within a standard cuvette. Low volume <0.5 μL gels become difficult to manipulate manually depending on handling procedures or geometries. After exposure to UV light, the hydrogel crosslinks and is covalently bonded to the coverslip to avoid any shifting of the sample during imaging.

The PEG hydrogel encapsulation process is a rapid, gentle, versatile, and inexpensive alternative mounting method useful for continuous long-term (e.g., several hour) imaging, in an open format, including imaging of neural activity across state changes, and for other applications requiring immobilized organisms, such as microinjection or laser ablation.

In some embodiments, the encapsulation process takes only minutes, with gelation occurring within seconds, trapping the organism within a confined space. Some encapsulated animals can push against the hydrogel and move or rotate slightly. The amount of organism movement within the hydrogel cavity may be tuned by applying different solutions that rapidly diffuse into the hydrogel. For example, transient exposure to standard paralytic chemicals can restrict micron-scale movements within minutes. For example, the movement index (MI) of $C.$ $elegans$ embedded in 20% PEG hydrogels was reduced 5-fold by exposure to the paralytic reagents sodium azide or tetramisole, both when applied during gelation and when applied transiently after encapsulation (from MI=0.33±0.21 to 0.07±0.01, and 0.06±0.02, respectively; P<0.0001). MI is an image-based difference index sensitive to lateral rotational movement, changes in focus, and photobleaching, as shown in FIG. 5. Photobleaching observed when using sodium azide contributed a majority of the MI compared with tetramisole.

Alternatively, a paralytic-free immobilization method that temporarily reduces the organism's body size in hyperosmotic solutions before crosslinking, tightening the hydrogel and immobilizing the organism as effectively as chemical paralytic agents. Buffer osmolarity can change body size, shrinking animals in hyper-osmotic solutions over the course of minutes through the loss of water. Animals encapsulated in a hyperosmotic solution before or during gelation shrink, thereby reducing the encapsulation space and tightening their confinement upon return to normal osmolarity and body size. Animals in a hyper-osmotic solution of 0.5 M glycerol (500 mOsm) or 1.5×SBasal buffer (420 mOsm) for 10 min prior to or during crosslinking, then imaged in normal osmolarity S-Basal buffer, were well immobilized (8±7 μm range, MI=0.02±0.007 and 15±9 μm range, MI=0.07±0.05, respectively). The hydrogel encapsulation method, with hyperosmotic pre-exposure, can serve a wide variety of imaging modalities and biological applications.

Hydrogel structures can be formed with any micron-scale geometry, including external and internal structures. Hydrogel molds can be created using micropatterned molds, embedding 3D channel structures, and by UV lithography to selectively crosslinking the hydrogel polymer. In some embodiments, this application offers the possibility to rapidly and more precisely deliver solutions to stimulate a wide variety of embedded and immobilized living organisms using imaging techniques that were not previously compatible. The hydrogel can be patterned by depositing a volume onto micron- to centimetre-scale raised features and crosslinked. The resulting gel can be removed yielding the positive mask of features to be used for orienting organisms in resulting patterns, shapes, or orientations. In some embodiments, microstructured silicone molds can be used, such as those fabricated from poly(dimethylsiloxane) or PDMS. However, high resolution patterning with oxygen-permeable molds (such as PDMS) requires transient removal of oxygen from the hydrogel liquid such as by addition of oxygen-scavenging chemicals like sodium sulfite. Alternatively, micropatterning microfluidic channels and bonding to various surfaces may also be accomplished for developing more well-defined features as described, or alternatively by masking UV light projected onto a hydrogel surface for lithography-like development of microscopic features and controlled immobilization of organisms.

One application of embedded hydrogel microfluidics is rapid chemical stimulation of immobilized living organisms, for example to observe biological or neural responses to drug exposure or direct excitation of chemosensory neurons. Hollow micron diameter channels at mm to cm lengths can also be created within the hydrogel material by embedding threads, sutures, or wires, then removing them after crosslinking. These channels can be as small as 20 to 40 microns in diameter. They can be interfaced with standard microfluidic inlets and outlets to control flow of liquids entering and exiting the channels, and chemicals diffuse from the channel(s) and propagate through the gel to the organism. With separation distances of tens of microns, sub-second switching is possible. An alternate approach is to flow liquids in PDMS or glass microfluidic channels just adjacent to the hydrogel and embedded live animals (FIGS. 1A-1F).

Figure 12A:
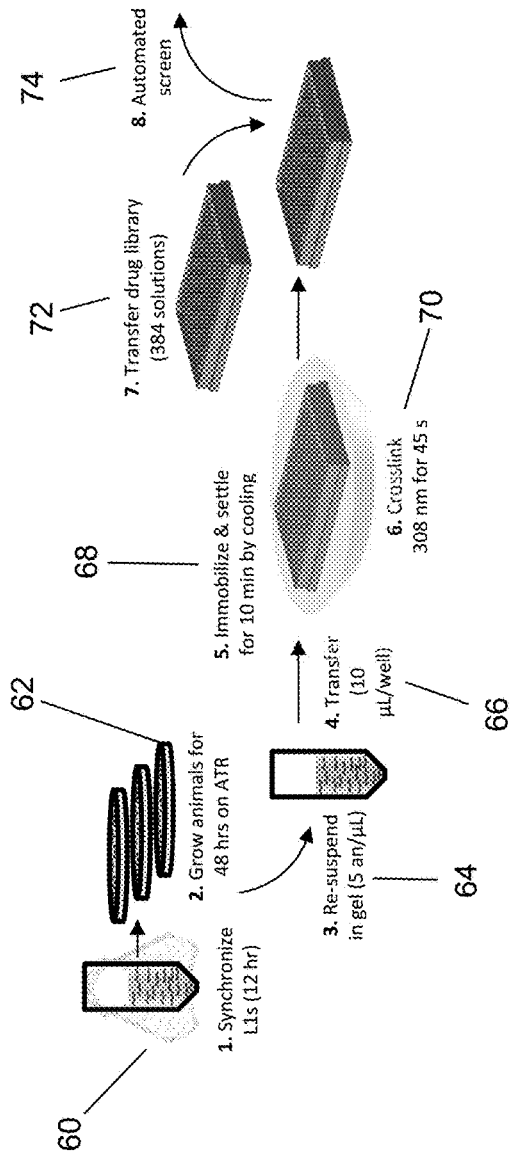
FIGS. 12A-12F shows an automated neuromodulator screening method by gel immobilization, optical stimulation and recording.

One application of this method is image-based automated screening of individual organisms that are measured at least 2 times points or at one time point for an extended exposure duration. In some embodiments, the samples can be immobilized for proper registration across time points or to prevent the occurrence of blurring in the image. For example, the PEG-DA hydrogel immobilizes a number of $C.$ $elegans$ (1 to >40 animals) in each well of a multi-well plate to screen for optical changes over time when exposed to different chemicals. For example, FIG. 12A-FIG. 12D show an automated in vivo neuromodulator screening method by gel immobilization, optical stimulation and recording. FIG. 12A shows the general procedure for filling and preparing a well plate to use in the automated experiment.

One example of the method observes the change in fluorescence of a reporter. A $C.$ $elegans$ model of Huntington's Disease was previously developed to cause abnormal protein aggregation in vivo, the main characteristic of this disease in humans. To detect the growth and suppression of these clusters, $C.$ $elegans$ strain(s) PolyQ24 AM138 rmIs [unc-54p::Q24::YFP], PolyQ35 AM140 rmIs132[unc-54p::Q35::YFP], and PolyQ40 AM141 rmIs132[unc-54p::Q40::YFP] (Mondal S. et al. Large-scale microfluidics providing high-resolution and high-throughput screening of *Caenorhabditis elegans* poly-glutamine aggregation model. Nat. Commun. 7, 13023 doi: 10.1038/ncomms13023 (2016)) can be constructed to express aggregated protein clusters as yellow spots throughout the animal's body, which can be observed and quantified at different points in time in the presence of therapeutic compounds. A compound that causes these yellow spots to decrease may serve as positive hits in a screen of many therapeutic drugs. Localization or intensity of fluorescent reporters are commonly used to detect molecular and genetic changes in live organisms and cells, with many other strains, cells, and organisms readily available to test in a similar manner. The hydrogel immobilization technique and automated image-capture cycling program can facilitate the collection of time-dependent changes in fluorescent signals in the presence of hundreds of different compounds, which is not yet possible without this method. Worms or samples may also be recovered from individual wells for further propagation, as well as genetic or molecular quantification and analysis.

A further application of this method is for screening functional modulators of neuronal activity in embedded whole organisms, like *C. elegans*. An example of such a screening method is an automated method of screening 384 different compounds to examine their effects on neuronal activity (calcium signals) in biological samples. An integrated strain of *C. elegans* that co-expresses Chrimson (a red light shifted channelrhodopsin) and GCaMP (a genetically encoded calcium sensor) in the AWA chemosensory neurons was developed in connection with this method, which enables stimulation and recordation of calcium activity in the same neuron over time (>24 hrs of repeated stimulation) as in FIG. 12C. This organism allows identification of drugs that affect neurotransmission between neuron depolarization and intracellular calcium release (e.g. drugs that affect voltage-gated calcium channels). By separating the excitation neuron (expressing Chrimson, or similar) and the readout neuron (expressing GCaMP, or similar), the screens can be made sensitive to drugs specifically affecting chemical synaptic transmission, gap junction transmission, or neuropeptide transmission. Genetic mutation that eliminate (or create new) information pathways between neuron pairs can make drug screens more selective.

Since the animals can survive immobilized in hydrogel for at least 24 hours, time-dependent effects of all compounds can be observed. Animals can be treated for t=0 hrs to show no effect, then treated with compounds and automatically screened to test at t=6, t=12, t=18 . . . to t=24 hrs, or at any point in time, at various time points, depending on the number of wells being screened. For example, a typical experimental duration for one well is 15 s (with 5 s red light pulse from 2.5-7.5 s), and the time for switching between wells is <1 s. The timing (duration, and cycles) and position settings can all be customized through a software suite, for example, based in MicroManager (FIG. 17).

Figure 12B:
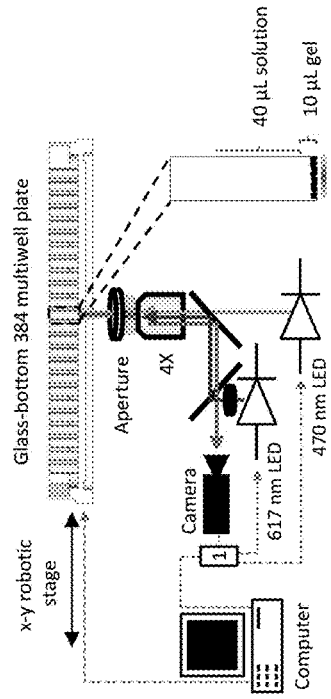
Figure 12D:
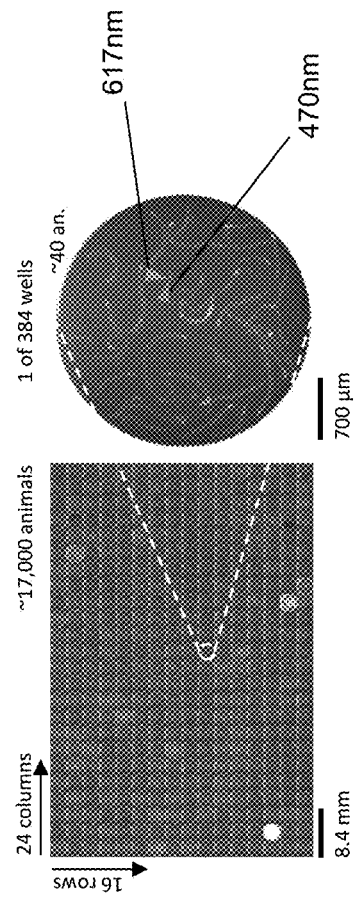
Figure 12C:
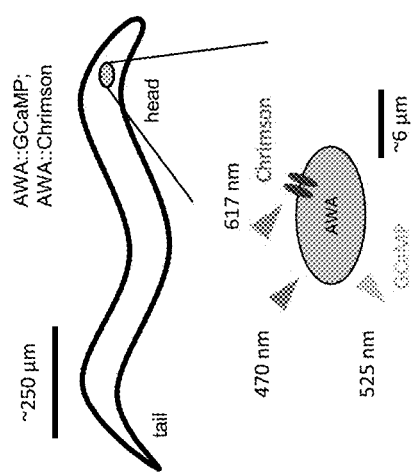
Figure 12F:
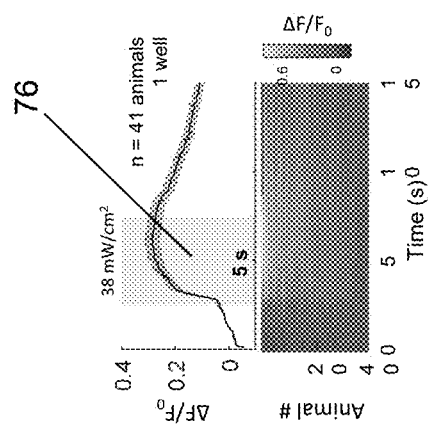

By immobilizing these *C. elegans* at the bottom of each well in a 384 multi-well plate with the included PEG-DA hydrogel (10 µL) FIG. 12D, it is possible to observe their neurons and calcium responses to red-light induced depolarizations, FIG. 12F. Because the hydrogel is permeable to small-molecules, animals may be treated with all-trans retinal (ATR) directly in the plate (essential for opsin function) FIG. 14, while compounds of choice (or from a library, FIG. 15) can be added. These molecules permeate the gel and are absorbed into the animals, eliciting responses in targeted neurons upon red light stimulation while simultaneously observing neural responses via the green light emitting calcium sensor. Additionally, immobilization allows for the same individual and position to be observed at various points in time.

Figures 2A, 2B:
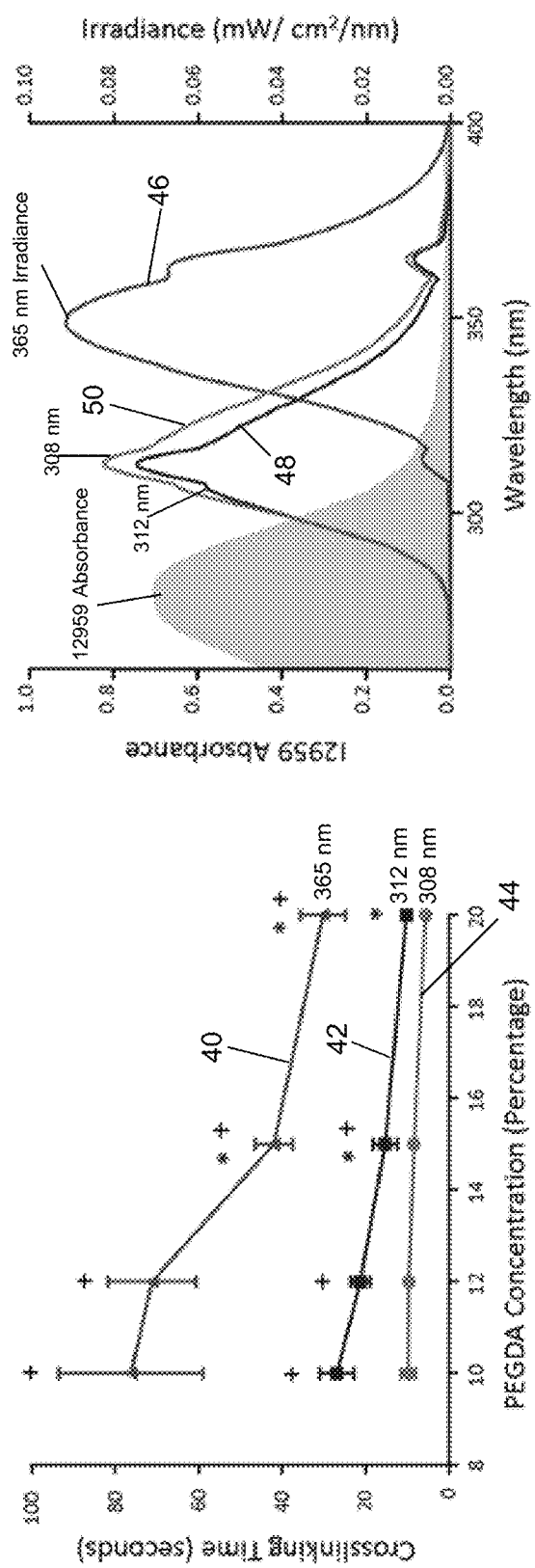
FIG. 2A and FIG. 2B shows characterization of PEG hydrogel crosslinking time at PEG-DA concentrations of 10%, 12%, 15% and 20% with UV sources of different irradiance spectra.

This method may utilize a custom optical configuration in which red light excitation (605-635 nm) is sent through an imaging objective (4×) at specified durations, along with pulsed blue light (488 nm, 3-10 ms pulses). These settings and durations can all be customized through a software suite, such as MicroManager (shown in FIG. 17). FIG. 2A also illustrates detailed spectral excitation/emission plots. Alternative wavelength combinations are appropriate for different optical reagents (FIG. 2B).

The methods described above could be expanded on towards various applications with all variables, limitations, and experimental conditions considered, including: calcium-based reporters, other fluorescent reporters, z-depth, immobilization, time-dependency, signal measurement, and sample size. The concept of spectrally-separated optogenetic activation and readout, e.g red-light activation and recording with GCaMP, could be paired between any neuron(s) of choice, or muscle-neuron, neuron-muscle, cell-cell, organ-cell, cell-organ, etc. This dual-imaging approach has been applied to various cell culture systems and model organisms, and could be applied here. Separately, but related to this image-based screening application, observation of time-dependent effects of any fluorescent or brightfield contrast picture/video without optogenetic stimulation is possible. Instead of recording video, taking a single image per well of an immobilized sample repeatedly across 384 wells can enable the potential to screen small-molecule effectors of translocation of fluorescent indicators, or even baseline change in fluorescence in the same well-plate sample position over time.

Additionally, all methods and applications described above could be expanded on in scale. Multi-well plates (from 6 to 1536 wells) could be adapted for screening based on the objective for recording (2.5×-40×), and desired sample and experimental conditions.

Parallelization of data acquisition could also be considered, for example, by imaging 4 wells at a time of a 1536 well plate using the same 4× objective as used for one well of a 384 well plate.

All of the applications described above can be applied to various other biological samples, cells, organisms, etc.

Examples

The systems and methods of the present disclosure are described in the following Examples, which are set forth to aid in the understanding of the disclosure, and should not be construed to limit in any way the scope of the disclosure as defined in the claims which follow thereafter. The following examples are put forth so as to provide those of ordinary skill in the art with a complete disclosure and description of how to make and use the embodiments of the present disclosure, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Materials and Methods
Strains and Culture

Nematode strains were grown on Nematode Growth Medium (NGM) plates seeded with OP50 bacteria. *C. elegans* were imaged as young adults and synchronized by picking L4 stage worms 24 hours prior the experiment and transferring them to seeded plates. Alternatively, L1 larval stage animals were picked individually from mixed-stage plates. The following strains were used: QW1217 (zfIs124 [Prgef-1::GCaMP6S]; ofIs355[Prab-3::NL SRFP]), with pan-neuronal expression of nuclear-localized GCaMP and mCherry (Venkatachalam et al., 2016), and NZ1091 (kyIs587[Pgpa-6::GCaMP2.2b, Punc-122::dsRed]; kyIs5662 [Podr-7::Chrimson::SL2::mCherry, Pelt-2:: mCherry]), which expresses the Chrimson ion channel and GCaMP calcium indicator in the AWA neuron pair (Lagoy et al., 2018) integrated from CX16573 (Larsch et al., 2015). For optogenetic stimulation, L4 stage animals were transferred to agar plates containing 50 µM all-trans retinal (Sigma-Aldrich) overnight unless otherwise described.

*I. paradoxus* pygmy squid adults were collected from sea grass beds in Nagoya, Japan and shipped to the Marine Biological Laboratory (Woods Hole, United States), where they were maintained in aquaria for several months before dying of natural causes. Mature animals readily mated and laid egg masses, with embryos hatching after one week to produce actively swimming and hunting squid larvae. While invertebrate care is not regulated under the US Animal Welfare Act, care and use of *I. paradoxus* in this work followed its tenets, and adhered to EU regulations and guidelines on the care and use of cephalopods in research.

Preparation of Materials for Hydrogel Embedding

PEG hydrogel solutions were prepared by combining 10%-20% w/v poly(ethylene glycol) diacrylate (PEG-DA, 3350 MW, ESI BIO) with 0.05%-0.10% w/v Irgacure 2959 photoinitiator (2-hydroxy-4'-(2-hydroxyethoxy)-2-methylpropiophenone, I2959, BASF) in deionized water (diH2O) or 1×S-basal buffer (100 mM NaCl, 50 mM $KPO_4$ buffer pH 6.0). A clean 1"×3" glass slide (VWR Micro Slides) was rendered permanently hydrophobic by exposure to vapors of (tridecafluoro-1,1,2,2-tetrahydrooctyl) trichlorosilane (Gelest) under vacuum for 1 hour, or temporarily hydrophobic by wiping with Rain-X Glass Water Repellent. Glass slides were cleaned with ethanol and water, then dried by air gun. For covalent attachment of hydrogels to glass, #1.5 cover slips (Thermo Scientific) were silanized by coating with 3-(trimethoxysilyl)propyl methacrylate (Sigma-Aldrich) (21 mM in ethanol) for 3 min, followed by ethanol wash, water rinse, and air dry. Treated glass slides can be prepared months in advance. Spacers were prepared by casting polydimethylsiloxane (PDMS, Sylgard 184, Ellsworth Adhesives) in a 1:10 (curing agent:base) ratio to thicknesses of 100, 200, and 500 μm.

Embedding Live Animals in PEG Hydrogel

A small volume (1-20 μL) of PEG hydrogel solution with photoinitiator was pipetted onto a hydrophobic glass slide flanked by two PDMS spacers whose thickness matched the desired hydrogel thickness. Animals were transferred into the hydrogel solution by worm pick and optionally cooled on ice or in a freezer to slow animal movement. A cover slip, untreated or silanized, was placed over the hydrogel droplet and supported by the spacers. The glass slide/cover slip sandwich was then placed over a UV light source and illuminated until gelation, for example for 5-100 seconds (depending on lamp power and hydrogel concentration). The sample was either observed immediately or the hydrogel disk was exposed by lifting the cover slip and adding a drop of aqueous solution over the disk. Hydrogel disks could be transferred to wet agar dishes to keep embedded animals hydrated.

Manual Embedding of Animals in PEG Hydrogel for 384 Multi-Well Plate Method

A small volume (10 uL) of PEG hydrogel solution (10% with 0.5×S. basal) with photoinitiator was pipetted into each PCR tube (one tube per one well). Young adult animals (CX16573) were transferred into the hydrogel solution by worm pick (up to 40 or more). The hydrogel and worm solution was transferred from one PCR tube to the bottom of one well of a 384 well plate, and repeated for as many PCR tubes prepared. The 384 well plate was placed into −20° C. freezer for no more than 10 min, then immediately placed on the 308 nm light source to crosslinking for no more than 45 s. Then, a small volume (60 uL) of 1 mM ATR in water was pipetted into crosslinked wells, covered, placed in the dark, and allowed to incubate for at least 1 hr, or up to 24 hrs. Animals were then imaged on a custom designed microscope and optical configuration allowing for both red-light excitation and blue-light excitation sent through the objective, all set by the initial experimental settings. Red light pulse durations, well position, cycle number and cycle delay conditions were set by a custom MicroManager script, and executed.

Manual Treatment of Multi-Well Plate Embedded Animals in PEG Hydrogel with Nemadipine-A After crosslinking and before all-trans retinal (ATR) transfer to each well, solutions of 10 μM, 50 μM, and 100 μM nemadipine-A to a final concentration of 1% DMSO in 1 mM ATR were prepared. A control well containing only 1% DMSO in 1 mM ATR was prepared as well. All solutions were added to individual wells, then time 0 was initiated and set to run an experimental cycle every 10 min for 24 hours using a custom MicroManager timing and position script, resulting in 144 15 s long videos for 4 independently treated wells. A slightly modified Neurotracker macro for 4× magnification was used to analyze each well at 100 min sampled time points. After experimentation, wells that were previously used were marked and not used again.

Automated Embedding of Animals in PEG Hydrogel for 384 Multi-Well Plate Method

Over 15,000 (NZ1091) eggs were synchronized by bleaching 8 100 mm nematode growth medium (NGM) plates, then starved in M9 solution and rotated at 20 C overnight (<30 hrs) to induce L1 arrest. Animals were then counted by a 10 uL sample and distributed equally to 100 mm seeded (dry 2 mL OP50) plates at 5000 animals/plate. Worms grew until young-adult age for 2-3 days at 20 C for 384 well plate deposition. Two to three days later, animals were washed with M9 into a 15 mL conical tube and centrifuged for 2 min at max speed (3000 rpm). The liquid-only suspension was gently removed by vacuum, while the remaining pellet and animals were resuspended with 10% PEGDA or M9 to 4 animals/uL concentration, enabling a theoretical final concentration of 40 animals/well. This minimum volume of 3,840 μL (ideally 4 mL containing 16,000 animals) was then evenly transferred to 8 wells of a shallow 96 multi-well plate, for automated transfer of 10 μL to each well of a 384 well plate using the Biomek 2000 MP200 tool and custom program. The multi-well plate containing animals was then placed at −20 C for no more than 10 min, then immediately crosslinked for no more than 45 s at 308 nm. A 10 s video of each well was automatically taken before animal crosslinking and after to demonstrate immobilization and scale of uniformity. A custom macro counted the number of animals per well based on a visible fluorescent marker in each animal, and montaged each video according to true positions of wells in the plate.

Automated Treatment of Multi-Well Plate Embedded Animals in PEG Hydrogel with Drug Library The crosslinked animal containing multi-well plate was then placed back on the Biomek 2000 workstation, and each well was automatically transferred 60 uL of ATR containing 50 uM of one compound from the small-molecule library with a 15 s delay, resulting in 384 different compounds screened in one final plate to more than 15,000 animals. One 15 s (2.5-7.5 s red light pulse) video per well every 100 min for 24 hours was recorded. The programmed 15 s delay in filling was used to align the drug exposure time with prior well experimental timing.

Synchronization of >17,000 *C. elegans* on all-Trans Retinal or Standard NGM Plates.

Over 17,000 animals were synchronized by scaling standard protocol volumes and using eight 100 mm NGM plates containing gravid adults (Stiernagle, 2006). For example, synchronization can be related to the age of the animals/organisms, or their length, weight, or size. Synchronized L1s were obtained by rotating prepared eggs adjusted to ~10 animals/μL at 10 rpm in M9 solution for 12-20 hrs at 20° C. The all-Trans retinal (ATR) plates were prepared by re-suspending pelleted OP50 *E. coli* to M9 containing a final ATR concentration of 50 μM. A 150 μL volume of this solution was seeded and spread onto each 100 mm plate immediately prior to adding 5,000 L1 synchronized animals (at ~10 animals/μL). Control non-ATR treated animals were similarly added to standard OP50 *E. coli* seeded plates. Worms were grown for ~48 hours at 20° C. until late L4 stage, then collected by washing off plates with M9. The final animal suspension was adjusted to ~10 animals/μL by centrifugation and resuspension in M9.

Hydrogel Embedding and Immobilization of Animals in 384 Multiwell Plates

For all well plate experiments, equal parts of 20% PEGDA (0.1% Irgacure) was added to a synchronized animal population in M9, resulting in ~5 an/μL, 10% PEGDA, 0.05% Irgacure, and 0.5×M9. A volume of 10 μL (containing ~40 animals) was delivered to each well of a standard high-content 384 multiwell imaging plate (Corning #4581) using a Biomek 2000 workstation (8 wells at a time), or manually transferred using a single or multichannel pipette. Both procedures used repeated mixing (4-5×) to maintain an even animal suspension during transfer. The animal-containing multiwell plate was transiently cooled for 10 min at −20° C. to settle animals at the bottom of the well, then immediately exposed to 308 nm UV light to photo-crosslink and embed the animals. Single wells can also be prepared by standard picking and transfer of animals to a final 10% gel solution (using PCR tubes), depending on experimental design or desired throughput.

Drug Library Preparation

Aliquoted LOPAC drug library plates were received from the UMMS small-molecule screening facility as 16 individual 96-well plates containing 3 nmol of compound per well (3 μL of 1 mM in 100% DMSO), stored at −80° C. until use. For a single 384 well plate screen experiment, four stock compound plates were thawed at a time and diluted with autoclaved diH$_2$O to 12.5 μM by adding 240 μL to each well using a Multidrop Combi Reagent Dispenser (Thermo-Scientific). Next, each well in the first column of the 96 well plate was manually aspirated, allowing for manual transfer of eight nemadipine-A positive drug controls, prepared manually yet exactly as described above (to contain four wells each with 10 μM and 100 μM concentrations). Then, a custom liquid handling robot protocol (Biomek 2000) was used to first mix each diluted compound 4×, then transfer 40 μL from each well to the 384 well plate containing 10 μL of worms embedded in gel. This resulted in a 10 μM final concentration of compound in 1% DMSO within each well. In total, this protocol allowed for screening of 384 different well preparations containing 320 different compounds, 56 buffer controls (1% DMSO), and 8 positive drug controls (nemadipine-A) in one automated experiment. The remaining diluted working concentration plates were stored at −80° C. for replicate use (with ~5 freeze-thaw cycles per plate). Nemadipine-A concentrations were prepared fresh or used after one thaw cycle. This protocol was repeated two times to screen eight plates containing 640 compounds from the Lopac small-molecule library, 122 1% DMSO buffer controls, and 16 nemadpine-A positive drug controls. One experiment costs <$100 ($38 for gel, $33/multiwell plate, $25/384 compounds).

Experimental Automation and Data Acquisition

After animal synchronization and initial plate set-up, the entire screening experiment functioned autonomously for hours to monitor up to 67,000 or more individual calcium response traces, using open-sourced software and hardware. Two scripts, GUI and SCREEN, were developed in Micro-Manager to input user-desired experimental settings and to execute them, respectively. A previously established Arduino microcontroller and scripts were used to coordinate and synchronize timing of user-selected optical stimulation parameters, illumination settings, and image acquisition (Nobska Imaging) (Lagoy and Albrecht, 2018). Also, seven timing and stimulation parameters required initial user input to control parameters such as the duration of GCaMP recording per well, optical stimulus power, timing during recording, and number of stimulus repeats. The same sequence of stimulation and recording was repeated for all desired number of wells, with a programmed delay between stimulation, wells, and cycles. Finally, the SCREEN script executed the multiwell plate position and all experimental controls input by GUI. For each screen experiment, experimental settings and a logged history of plate position and timing data was saved for exact experimental replicates and meta-analysis. All camera acquisition sequences were also saved with date stamped indexed filenames for proper storage and streamlined analysis. Animals were imaged on a commercial microscope with robotic x-y axis stage (RAMM Frame, ASI) with custom optical configurations as previously described (Lagoy and Albrecht, 2018), allowing for simultaneous blue-light excitation (GCaMP monitoring) and red-light excitation (Chrimson stimulation) through the 4×/0.28 NA wide-field imaging objective. The set-up was slightly modified with adjustable in-plane apertures to ensure independent optical stimulation per well. All control software was developed using MicroManager's open-source platform, as described in the Results. Experimental conditions (i.e. camera settings and experimental control) are initially configured using a custom graphical user interface (GUI), and executed using a custom script to automate synchronized stage positioning with stimulation and recording (SCREEN). Default camera settings were 100 ms exposure, 5 ms pulse, 5 ms delay, 2×2 binning, at 1024×1024 resolution, and 15 s TIFF stack movies were recorded per well with one 5 s red light pulse (35 mW/cm2) from 2.5 s-7.5 s. All experimental settings, run-time metadata, and videos are logged and saved in real-time with date and time as well as well position, cycle number, and movie number on file names for streamlined processing, indexing, and set-up of exact experimental repeats.

Analysis Structure and Calcium Response Quantification

Throughout each automated experimental duration, TIFF stacks were collected automatically using control software as described above. Videos were stored, processed, and analyzed using either a semi-automated (blue arrow path) or completely automated method (black arrow path) with both increased data accuracy and slower analysis rate, or vice versa, respectively. The semi-automated method employs a custom user-friendly ImageJ script that prompts manual selection of animal neuron positions (X,Y pixel coordinates), recorded per well and saved as separate TEXT files. The average time for manual and trained selection of neurons (at 40 animals/well) was up to ~20 wells/hour, requiring ~20 hours per 384 well plate. Once all neuron positions are recorded for each well, the position files were used to extract coordinates for automatic recording of quantification parameters (like integrated density, background intensity, etc.) and saved on a new line in a TEXT file for each frame of each video, for all videos per well, and all wells. All processed videos were stored as TEXT files and read into MATLAB using tall tables and datastores for parallel processing, analysis, and visualization.

A suite of custom ImageJ macros was developed for automated neuron selection and trace recording (aNT), or to manually select neurons (neuronPos) and then record calcium intensity in each well across all wells and cycles automatically (NT). The neuronPos and NT scripts were used for all results described. Immediately after analysis, a custom ImageJ macro (oWells) was used to organize all videos for each well to their own well-labelled folders for simplified manual and automatic parsing of the large data. In both aNT and NT analysis scripts, a large 16×16 pixel square was used for measurement of integrated intensity (FR), which permitted slight animal movement during unsupervised analysis. Local background subtracted fluorescence (F) was calculated as $F=(F_R-F_{bg})$. A single absolute minimum value from all background subtracted values (|minimum F|) was then added to each raw fluorescence value (F) to correct for all situations where negative fluorescence (−F) occurred due to background subtraction errors. Change in fluorescence (ΔF/F0) was then calculated as $(F-F_0)/F_0$ where F0 is the mean fluorescence of all time frames before stimulation, unless otherwise stated or shown. All neuron positions and raw measured values were recorded for each video and animal, saved with corresponding text file names for streamlined analysis, organized data logging, and regeneration of figures from raw files. Neuron positions were selected using either the first or last video of each cycle. Another custom ImageJ macro (MWS) and FIJI Grid/Collection stitching plugin were used to stitch one frame from all full-resolution videos across a 384 well plate (24576× 16384 px), which was used for visualization and quality control.

All-Trans Retinal Exposure Duration and Dose Response Characterization in Multiwell Plates To wells of embedded animals synchronized using either ATR or non-ATR NGM plates prepared as described above, solutions of ATR at final concentrations in each well were made to 0 μM, 0.1 μM, 1 μM, 10 μM, 100 μM, or 50 μM containing 1% DMSO. Three replicates of each condition were set-up in adjacent wells (block form). The GUI script was configured to automatically stimulate and record animals in each well every 20 min for ~24 hrs (cycle 72×, 20 min cycle delay) with different initial delay timing or trigger periods. Neuron positions were manually selected then ΔF/F0 was automatically quantified (using neuronPos and NT ImageJ macros) as described previously.

Automated Small-Molecule Screening

For each prepared 384-well plate containing multiple control conditions (56 1% DMSO buffers and 8 nemadipine-A drug controls) and 320 different compounds, 15 second TIFF stack movies (10 fps) were recorded for each well, with 1 second stage positioning delay between wells, and repeated every 257 min for ~18 hours of drug exposure. This protocol resulted in 4 videos per well at equally timed 6 hour intervals (1,536 videos per plate experiment, and 3,072 videos total for all 768 wells screened). Default camera settings, experimental control, and plate positions were configured as described above using the GUI and executed using the SCREEN scripts. This data size accumulated to ~1 terabyte containing over 20 million neural trace data time points. When combining multiple screening plate datasets, a relative scaling factor was used to standardize for control responses.

Data Processing, Statistical Comparisons, and Visualization

All data was processed using custom developed scripts and parallel processing in MATLAB2017a to handle large (tall) data sets. MATLAB2017a was also used to perform each one-way analysis of variance (ANOVA1) with Bonferroni's method of multiple comparisons (* $p<0.05$,  $p<0.01$, * $p<0.001$). Comparison bars without asterisks are the same significance level for simplicity. Two-way repeated measures mixed analysis of variance with Bonferroni's method of multiple comparisons was used to compare repeated measures across more than groups (** $p<0.01$) using IBMs SPSS.

Recovery of Treated and Stimulated Animals from Embedded Gel in Wells of 384 Well Plate C. elegans that were embedded in 10% PEGDA of a 384 well plate are recoverable by first swirling a 200 ul tip in the well then transferred (30-50 ul) multiple times to an agar plate (seeded or unseeded) until no gel or animals were seen in the well. These animals can be kept for propagation of compound-treated effects, and recovery of observed animals from wells is typically 100%. Quantification of effects could include, but are not limited to brood size quantification or F1 phenotypic effects (length, movement, behavior, etc.). Later generation progeny could also be tested for epigenetic or hereditable effects in the same multi-well embedding and recovery format.

Mounting Animals for Observation with Differential Interference Contrast (DIC)

For hydrogel encapsulation, 5 μL of a 10% PEG hydrogel with 0.1% I2959 containing late L1/L2 stage animals was placed on a fluorinated glass slide with 50 μm thick tape spacers, polymerized with 312 nm UV light, and imaged on an upright Zeiss Axioskop microscope with a 100×/1.4 NA objective using DIC optics. Images were captured every hour for 12 hours without movement of the sample. For comparison, animals were mounted onto conventional agarose pads with chemical or physical restraint. In azide paralysis conditions, 1-5 μL drop of S-Basal buffer with 25 mM sodium azide was placed on a 1% agarose pad that also contained azide. Animals were picked into this droplet and a cover slip was placed on top before imaging. Alternatively, a 0.25-0.5 μL drop of polystyrene nanobeads (100 nm, Polysciences, Inc.) was placed on a 10% agarose pad prior to adding animals, a cover slip, and imaging.

Recovery of C. elegans from PEG Hydrogels

Young adult worms were embedded in 5 μL 20% PEG hydrogels with 0.1% I2959 by crosslinking for 15 s at 312 nm on an unsilanized glass slide with 100 μm tape spacers. Hydrogels were transferred to an agar plate to keep hydrated and were stored at room temperature (22-23° C.). After 24 hours, hydrogels were separated with tweezers and animals were scored for viability (movement and pharyngeal pumping). Some animals were transferred to cover slips with 1% agarose pads for imaging.

Characterization of Light Sources and Crosslinking Conditions

Several ultra-violet (UV) light sources were used for crosslinking the hydrogel: a gel box transilluminator at 308 nm (Hoefer Scientific Instruments, model UVTM-25) and two hand-held compact UV transilluminators, at 312 nm (International Biotechnologies, Inc, model UVH, 12 W) and at 365 nm (UVP, model UVGL-15, 4 W). Light power was measured with a power meter (Thorlabs PM100) and 200-1100 nm sensor (Thorlabs S120UV) placed directly on the light source or on a glass slide or cover slip. Power values were converted to irradiance by dividing by the area of the 9.5 mm diameter sensor. Illumination spectra were obtained using a spectrometer (mut GmbH TRISTAN) with a fiber light guide (200-1100 nm range, 400 μm diameter). The photoinitiator absorbance was obtained with a spectrophotometer (Thermo Scientific Multiskan Spectrum).

The hydrogel crosslinking time was determined optically by monitoring movement of young adult worms during crosslinking. Gels of varying PEG-DA concentration, photoinitiator concentration, and geometry (spacer thickness and volume) were compared for each light source. Videos were captured at 1 frame/s using a Leica S6D stereoscope, converted to reflectance illumination by replacing one eyepiece with a white LED lamp, and recording via the opposite eye path with a UniBrain Fire-I 580c camera. Animal movement was analyzed by comparing frame-to-frame image differences in ImageJ. Crosslinking time was determined as the time until image difference measurements reduced to within 1 standard deviation of noise, and verified visually during observation of videos.

Quantification of Movement of Hydrogel-Embedded Animals

Young adult QW1217 worms with pan-neuronal expression of nuclear-localized mCherry were embedded in 10% and 20% PEG hydrogels (3 µL with 100 µm spacer, 0.1% I2959, 20 s exposure using a 312 nm UV source). Worms received either no pretreatment, exposure to hypoosmotic (diH$_2$O, 0 mOsm) or hyperosmotic buffers (0.5 M glycerol in diH$_2$O, 500 mOsm or 1.5×S-Basal, 420 mOsm) for 10 min, or cooling in a −20° C. freezer or in contact with ice for 1-3 min prior to crosslinking. PEG hydrogel solutions were prepared in diH$_2$O or S-Basal buffer, and some contained the paralytic reagents 25 mM sodium azide (Massie et al., 2003) or 1 mM tetramisole hydrochloride (Sigma) (Larsch et al., 2013). Other hydrogel solutions were prepared in 500 mM glycerol or 1.5×S-Basal hyperosmotic buffers. After crosslinking, all hydrogels were submerged in an aqueous solution of either S-Basal, diH$_2$0, sodium azide (25 mM) or tetramisole (1 mM) for imaging. Videos were captured with a Hamamatsu Orca-Flash 4.0 camera at 1 frame/sec for 3 min on a Zeiss AxioObserver inverted epifluorescence microscope with a 20×/0.5 NA objective.

Animal movement was analysed by comparing frame-to-frame image differences. Movement index is described using the equation M.I.=$\Delta I_{ROI}/I_{ROI}-I_{BG}$, where $\Delta I_{ROI}$ represents the difference in pixel intensity between consecutive frames, averaged across a region of interest (ROI), $I_{ROI}$ represents the average intensity of the ROI, and $I_{BG}$ represents the average intensity of a Background region. High- and low-movement examples show the timecourse of instantaneous movement. First, the absolute value differences between each pair of consecutive frame averaged pixel intensities were calculated. Next, the difference image stack was smoothed (average of its 3×3 neighborhood). To reduce the contribution of pixel noise, a value of 10 (corresponding to average pixel noise) was subtracted uniformly from each frame and negative values were set to 0. Regions of Interest (ROIs) were selected over the head (nerve ring) and ventral cord and a background region (BG). The movement index was calculated as M.I.=$\Delta I_{ROI}-I_{BG}$, where $\Delta I_{ROI}$ is the mean of difference images across the ROI, and $\Delta I_{ROI}$ and $I_{BG}$, are the mean intensity of the ROI and background regions for the first frame, respectively. Here, identical sequential frames would have a M.I. of zero, whereas images that have changes in position, rotation, focus, or intensity have increasing M.I. values.

Movement in the image plane was quantified by tracking cell nucleus position over 3 minutes. Individual neurons were tracked using NeuroTracker (Larsch et al., 2013) and centroid positions were used to determine the range of axial movement by the animal.

Long-Term Imaging of Optogenetically-Induced Calcium Transients Using 3D Light Sheet Microscopy Young adult animals co-expressing Chrimson and GCaMP2.2b in the AWA chemosensory neurons were embedded in a PEG hydrogel bonded to a 24×50 mm methacrylate-silane-treated cover slip. Animals were picked into a 2.4 µL drop of 13.3% PEG-DA solution with 0.067% I2959 in 500 mM glycerol in diH$_2$O. After 5 min, the sample was cooled on ice for 30 s and exposed to UV light for 30 s with a 308 nm handheld lamp. Cover slips were mounted into a light sheet chamber (ASI, I-3078-2450) and filled with ~5 mL diH$_2$O. The dual-inverted selective plane illumination microscope (diSPIM) recorded the calcium response of AWA with a 488 nm excitation laser (Vortran Stradus VersaLase) at 1 mW power setting and a 525/50 nm emission filter. Single-view volumetric stacks (40 slices with 1 µm spacing, 166×166×40 µm$^3$), were obtained at 1 volume/s for three 60 min recording sessions beginning at t=0 h, 6 h, and 13.5 h, for a total of 432,000 image frames. A red LED light (617 nm, Mightex, with 620/30 nm filter) was mounted either above the stage, illuminating the animals at a 45 degree angle, or from below with a 600 nm shortpass dichroic through a 4× objective, and controlled via MATLAB and an Arduino controller. Red light pulses, 10 s in duration, were repeated each minute during recordings. For each time point, the volume stack was compressed into a single maximum projection plane, and intensity values were integrated across ROIs surrounding each neuron or neuronal process. After subtracting background intensity from a nearby region, fluorescence intensity (F) integrated across the neuron or neurite ROI was normalized to the initial intensity averaged over 1 s (F$_0$). No interference was observed in background or neural ROIs during red light exposure.

Imaging of Living Pygmy Squid Using 3D Light Sheet Microscopy

Pygmy squid (*Idiosepius paradoxus*) at three days post-hatching were treated with 1 µM BODIPY 564/570 C$_3$ succinimidyl ester vital dye (ThermoFisher D2222) in filtered seawater for 1 hr to label cell boundaries and generally visualize morphology, modifying methods for the marine worm *Platynereis dumerelli* (Steinmetz 2007). Squid were washed five times in filtered sea water, then paralyzed by exposure to 3.75% MgCl$_2$ in sea water for 15 minutes and transferred to a hydrophobic glass slide. Excess sea water was aspirated by transfer pipette such that approximately 4 µL liquid remained. To this, 16 µL of 20% PEG-DA in sea water with photoinitiator was added and gently mixed. A methacrylate silane-treated 24×50 mm$^2$ cover slip was placed 1.2 min over the droplet using glass slides as spacers. The hydrogel was crosslinked by exposure to 365 nm UV light for 1 min. The coverslip was mounted into the light sheet chamber and filled with sea water. Dual-view volumetric stacks (30 slices with 1 µm spacing, 332×332×30 µm$^3$) were obtained using a 561 nm laser (4 mW power setting).

Hydrogel Crosslinking and Extrusion from Glass Microcapillaries

A solution of 10% PEGDA with 0.05% Irgacure 0.5×M9 was prepared. Next, 2 µL gel was pipetted onto a standard 1 mm×3" fluorinated glass slide. Several *C. elegans* were picked into gel drop. Then, a glass microcapillary (WPI #1B100F-4) was brought near the droplet and wicked up within seconds. To crosslink, a 312 nm UV light source exposed the sample for 45 s. Finally, a plunger (similar guage wire) was fit into the capillary and used to gently push out the crosslinked gel containing embedded and immobilized animals. Lastly, M9 buffer was used to submerge the extruded hydrogel to keep hydrated. This is the typical methodology used with other gels for standard light-sheet imaging, but this technique enables no paralytics or change in temperature to restrict movement and/or burrowing, which is typical by these animals.

Results

Immobilization of *C. elegans* within PEG Hydrogels

Figure 1F:
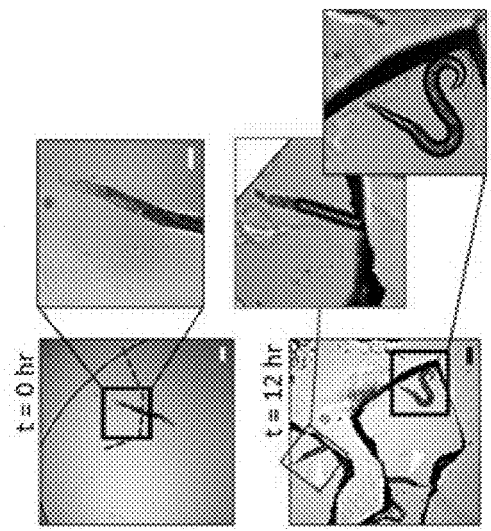
Figure 1E:
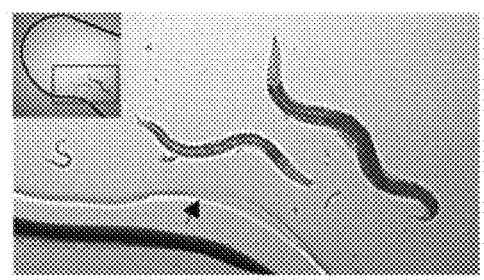

FIGS. 1A-1F show mounting live *C. elegans* 16 in hydrogels 10 and on agarose pads for microscopy. FIG. 1A shows the schematic of worm mounting procedures by PEG hydrogel encapsulation (left) or on agarose pads (right). FIG. 1B-FIG. 1D show images taken over 9 hrs in a 10% PEG hydrogel (FIG. 1B) or on agarose pads with 25 mM sodium azide (FIG. 1C) or 100 nm polystyrene beads (FIG. 1D). Solid vertical lines 20, 22, 24 indicates pharynx landmark position at t=0, dashed lines 26, 28, 30 indicate landmark position at each time point, and the arrows indicates displacement relative to t=0, with a scale bar of 10 µm. FIG. 1E shows multiple larval and adults stages embedded in the same hydrogel. The hydrogel edge is indicated by a faint line (shown with an arrow 32), surrounded by about 100-200 µm of uncrosslinked polymer (scale bar of 100 µm). FIG. 1F shows worms embedded in 20% PEG hydrogel that were imaged immediately after crosslinking and after release 12 hr later. Arrowheads indicate the cavity of the worm in the hydrogel (scale bars of 200 µm and 100 µm for the inset).

Encapsulation of animals in a PEG hydrogel 10 was accomplished by preparing a glass slide base 12 and cover 17, placing spacers 18 that determine hydrogel geometry onto the glass slide base, pipetting the hydrogel precursor solution, placing animals, such as the work 16, into the precursor droplet, covering the droplet with a cover slip 17, and crosslinking the hydrogel by brief exposure to light (FIG. 1A). During light exposure, the hydrogel 10 increases viscosity until gelation up to the surface of the embedded worm. After crosslinking, the animals were fully encapsulated in the hydrogel, preventing large movements beyond their encapsulated space (FIG. 1B). Encapsulation occurred within seconds and could last for days, as animals could not escape. The flexibility of animals and the hydrogel enabled some movement within this confined space during contraction of body wall muscles, mostly anterior/posterior translation along the body axis and less frequently axial rotation. Gravid adults could also lay eggs into the encapsulation space. Differential interference contrast (DIC) images at 100× magnification showed minimal change in cellular morphology in animals embedded in a 10% PEG hydrogel.

By comparison, conventional worm mounting requires melting agarose into a thin pad, picking animals onto the pad, adding a chemical or mechanical immobilizer, and covering with a cover slip (FIG. 1A). Animals exposed to 25 mM sodium azide, which inhibits mitochondrial function and thereby relaxes muscle tone, can take an hour or more to fully immobilize (FIG. 1C). Further, sodium azide-paralyzed animals displayed characteristics of necrotic cell death after 6 hours (Crook et al., 2013). Animals became immobilized with 100 nm polystyrene nanobeads more quickly than with azide, but they could still move gradually over hours (FIG. 1D). For effective nanobead immobilization, animals were compressed causing an apparent increase the width of the worm (Kim et al., 2013).

Animals of all stages, from eggs to larval stages to adults, could be mounted in the same hydrogel, a shown in FIG. 1E. Encapsulated animals were recoverable by breaking the hydrogel, for example, with gentle pressure from a worm pick or fine-point forceps (FIG. 1F). After 24 hours of hydrogel encapsulation, young adult *C. elegans* remained mostly viable; of 241 worms, 207 (86%) crawled away upon release.

Parameters Affecting PEG Hydrogel Crosslinking

FIG. 2A and FIG. 2B shows characterization of PEG hydrogel crosslinking rates at PEG-DA concentrations of 10%, 12%, 15% and 20%. FIG. 2A shows the crosslinking time determined by immobilization of young adult animals in 10-20% PEG-DA exposed with 365 nm (line 40), 312 nm (line 42), and 308 nm (line 44) UV sources. Each point represents n=10 independent trials, with each trial having n=2-5 worms per experiments. Values represent means (standard deviation). Statistics were performed using ordinary 2-way ANOVA with Bonferroni's post hoc tests for pairwise comparisons: *$P<0.05$ for each concentration compared to 10% PEG-DA, and +$P<0.05$ for each source compared to 308 nm UV. FIG. 2B shows the absorbance spectrum of 0.001% I2959 (black, left axis), and emission spectra for each UV exposure source (right axis). Line 46 represents 365 nm, line 48 represents 312 nm, and line 50 represents 308 nm UV sources. Emission spectra were normalized such that area under each curve matched total output power.

The mechanical, diffusive, and optical properties of PEG hydrogels can be tuned via monomer chain length and concentration (Bryant and Anseth, 2002; Choi et al., 2013; Mellott et al., 2001). To determine how gelation properties are affected by polymer concentration and other photocrosslinking parameters, we imaged animal movement during crosslinking and measured the exposure time at which motion ceased. Using several UV light sources, hydrogels of different size, monomer concentration, and photoinitiator concentration gelled in less than one minute with an irradiance dose of 15-220 mJ/cm$^2$ (FIG. 2A). Higher concentrations of PEG-DA reduced the required time of UV light exposure, with a 20% hydrogel gelling in about one-half the exposure time required for a 10% hydrogel.

Figure 3A:
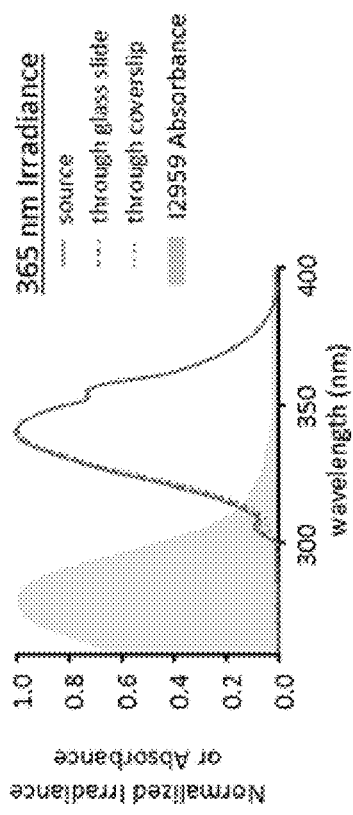
FIG. 3A, FIG. 3B, and FIG. 3C show irradiance of different UV light sources and substrates.
Figure 3B:
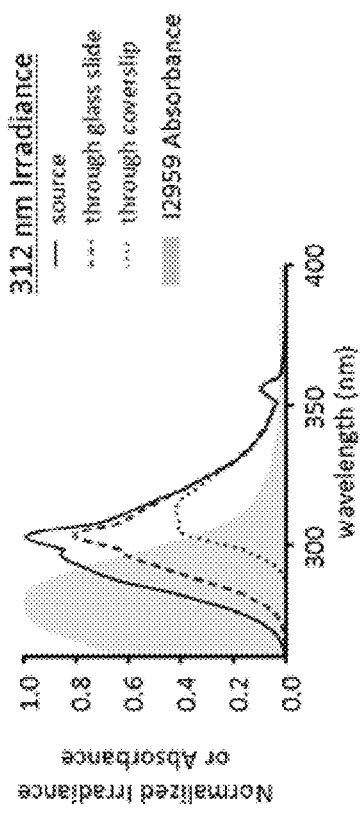
Figure 3C:
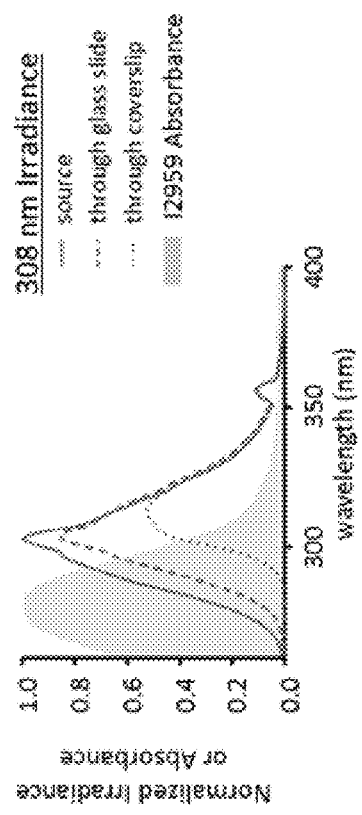

The intensity and wavelength of light exposure affects crosslinking rate. The absorbance of the I2959 photoinitiator drops rapidly above 300 nm (FIG. 2B) such that shorter wavelength UV sources crosslink the hydrogel more efficiently. For example, a 308 nm medium-wave UV-B transilluminator box gelled the polymer in 6-10 s at 2.6 mW/cm$^2$ (16-26 mJ/cm$^2$ dose), for 20%-10% hydrogel concentration, due to strong overlap between light emission and photoinitiator absorbance. Similarly, a 312 nm handheld medium-wave UV-B light required 12-25 s exposure at 2.2 mW/cm$^2$ (30-55 mJ/cm$^2$ dose). A 365 nm long-wave UV-A source required a longer exposure time of 30-70 s at 3.1 mW/cm$^2$ (95-220 mJ/cm$^2$ dose) for 20%-10% polymer concentration due to weak photoinitiator absorbance at this wavelength. Glass slides and cover slips that absorb strongly at UV-B wavelengths (FIG. 3A-FIG. 3C), such as those made from soda-lime glass and many plastics, require extended exposure times. FIG. 3A-FIG. 3C show irradiance of different UV light sources and substrates. Normalized absorbance spectrum of Irgacure 2959 photoinitiator and irradiance of each UV exposure source alone, through a glass slide, and through a glass coverslip. Irradiance curves for each substrate were normalized to the irradiance of each source at 365 nm.

Figure 4B:
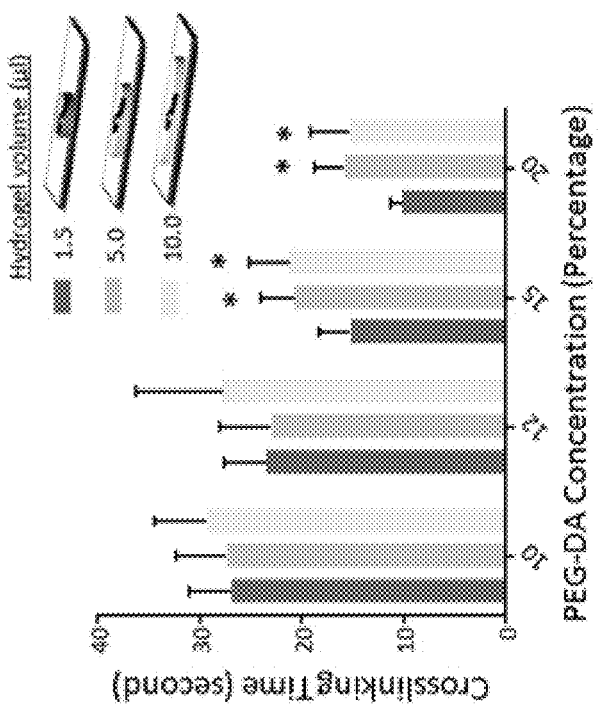
FIG. 4A, FIG. 4B, and FIG. 4C provide characterization of PEG hydrogel crosslinking for different PEG-DA concentrations, photoinitiator concentrations, and geometries.
Figure 4A:
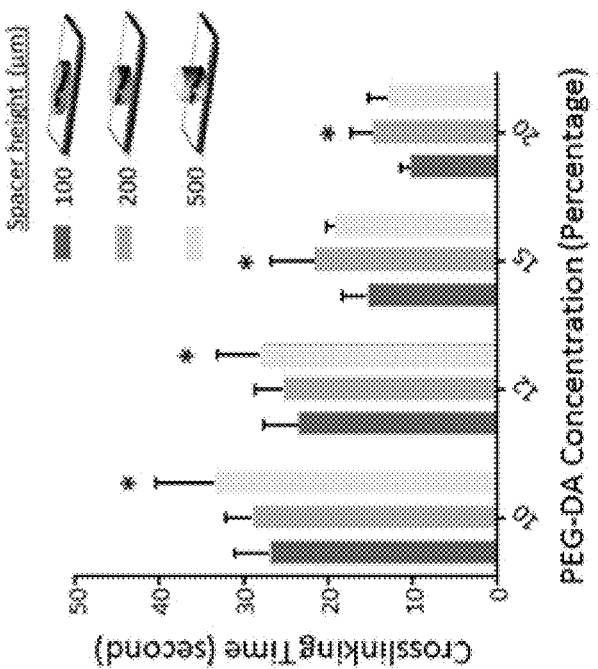
Figure 4C:
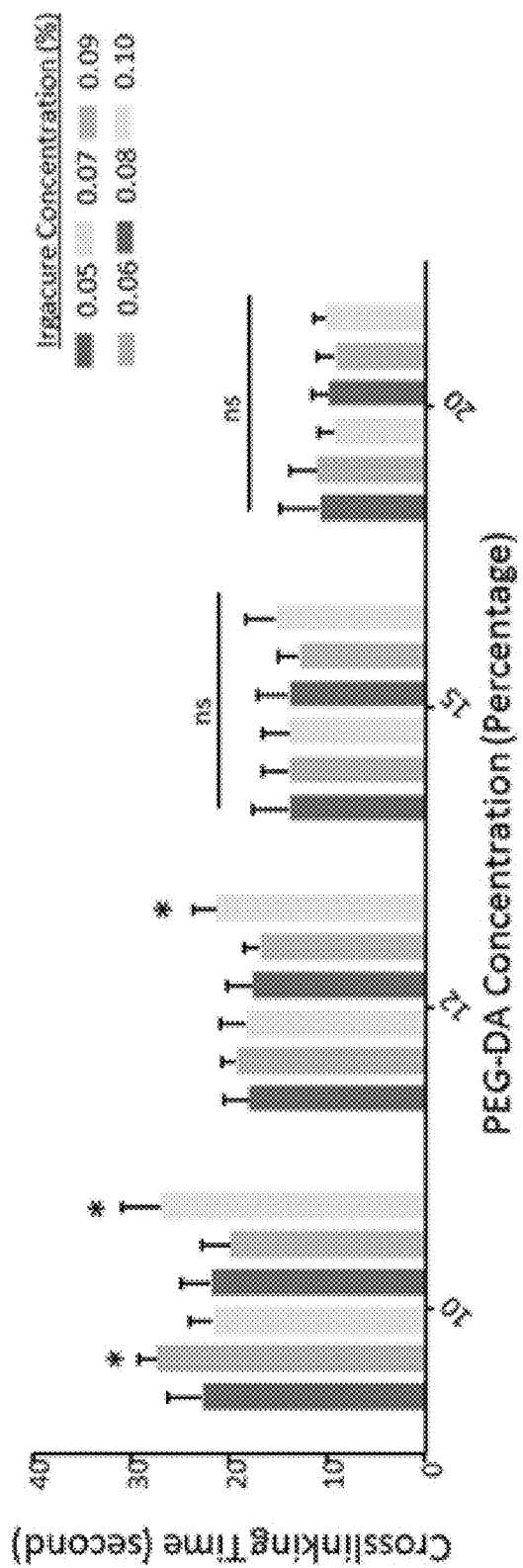

Hydrogel geometry had a minor effect on crosslinking rates. Thinner hydrogels (100 µm vs. 500 µm) and smaller hydrogels (1 µL vs. 10 µL) gelled slightly faster by less than 20% (FIG. 4A-FIG. 4C). FIG. 4A-FIG. 4C provide characterization of PEG hydrogel crosslinking for different PEG-DA concentrations. Each bar represents the average amount of time it takes the hydrogel to crosslink with various volumes (FIG. 4A), heights (FIG. 4B), and I2959 concentrations (FIG. 4C), exposed with 312 nm UV source. Each bar represents n=10 trials, with each trial being n=2-5 worms. Values represent means (standard deviation). Statistics were performed using ordinary 2-way ANOVA with Bonferroni's post hoc tests for pairwise comparisons, *P<0.05. Photoinitiator concentration did not affect cross-linking rate.

Effects of Buffer Conditions on Immobilization of *C. elegans* for Microscopy

Figure 6:
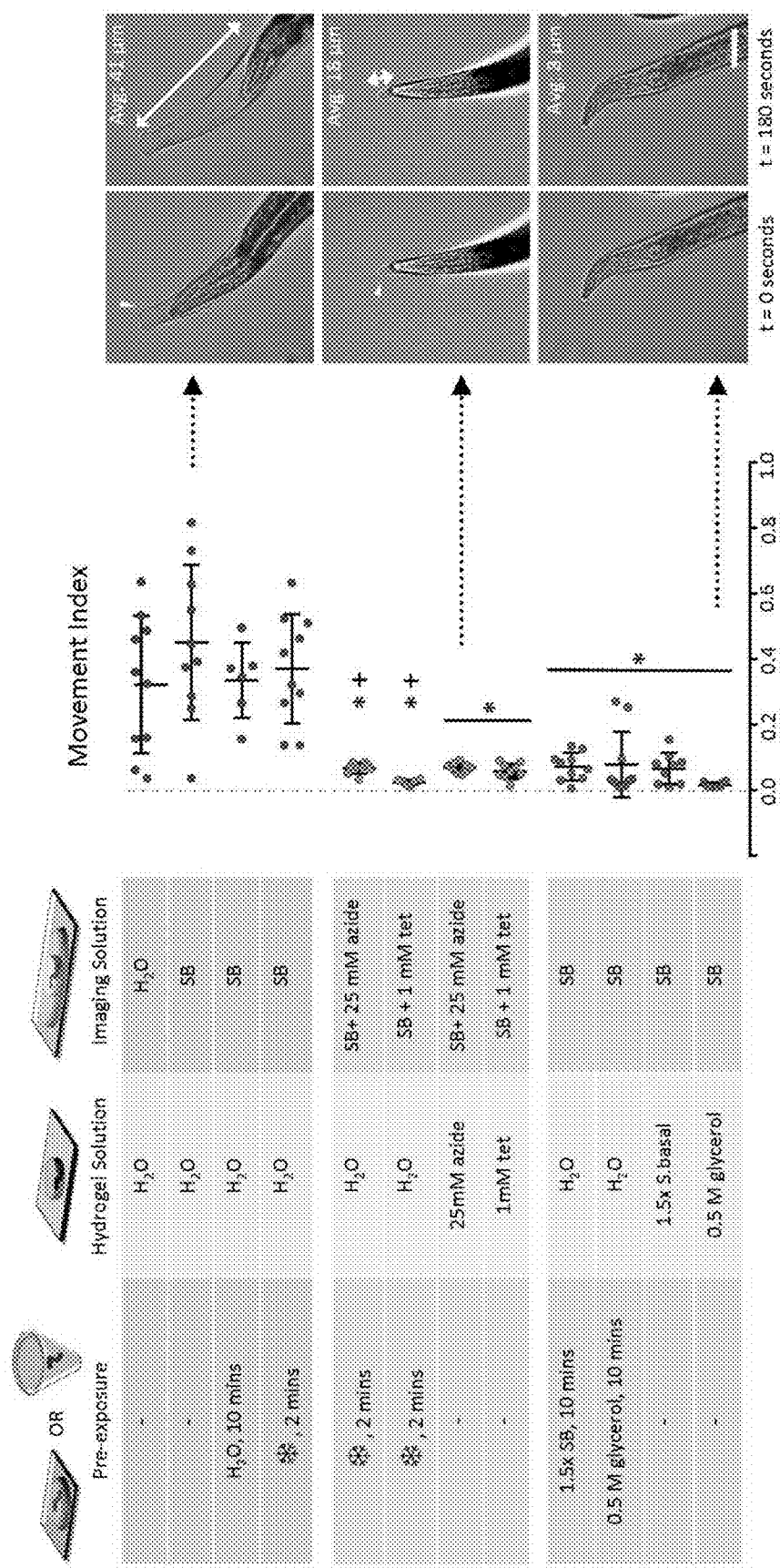
FIG. 6 shows immobilization quality (Movement Index) for different buffer conditions before, during and after hydrogel.
Figure 7:
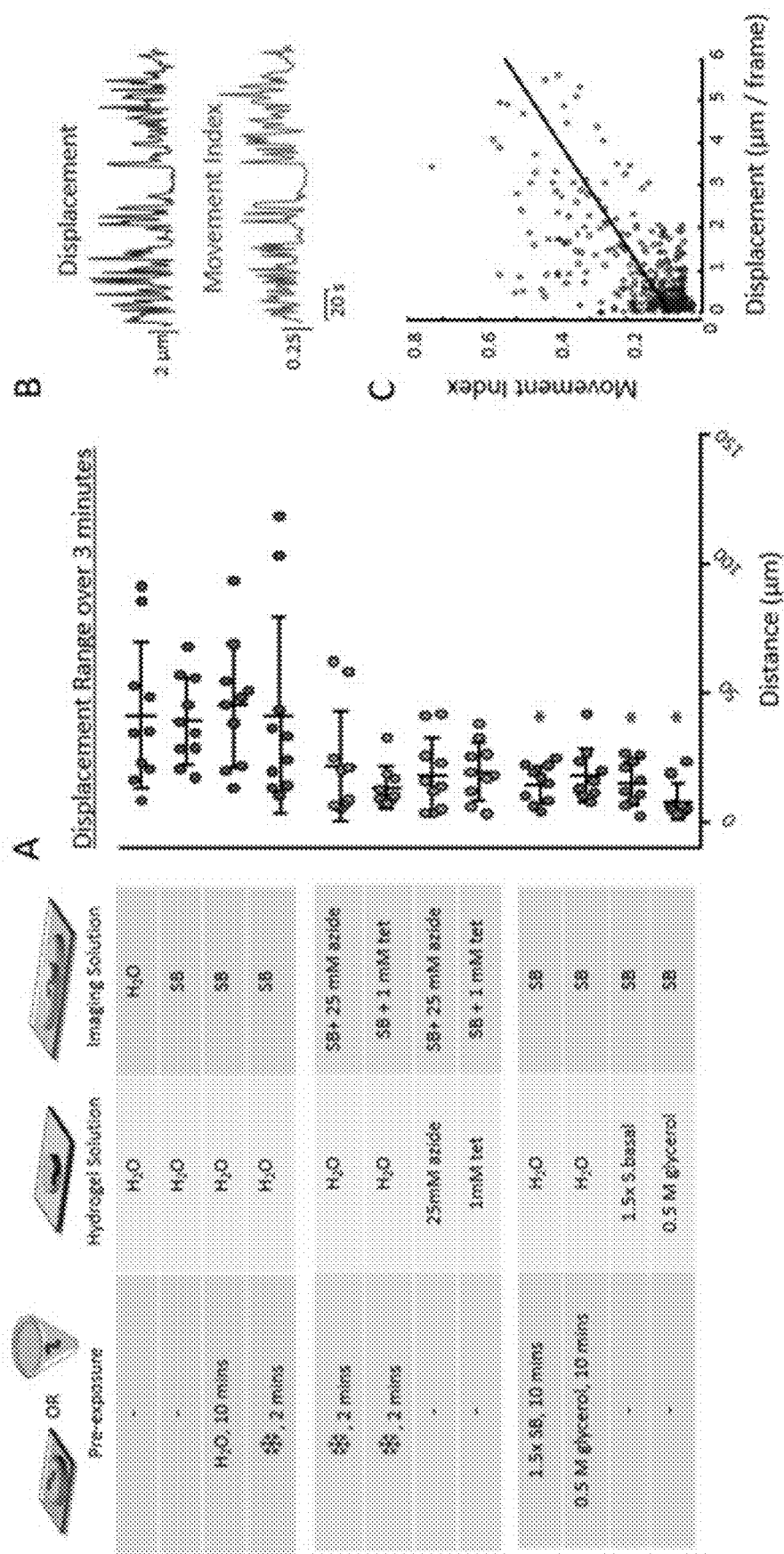
FIG. 7 shows displacement range over 3 minutes for animals embedded in different conditions before, during, and after hydrogel crosslinking.

FIG. 5 shows quantification of micron-scale motion by a Movement Index sensitive to translational, rotational, and intensity changes over time. FIG. 6 shows how buffer conditions before, during and after hydrogel crosslinking influence immobilization for microscopy. Pre-exposure to hypo- or hyper-osmotic solutions for 10 minutes, or cooling pretreatment (on ice or in a −20° C. freezer for 2 minutes) occurred in a droplet or microtube. Hydrogel solutions were prepared in water ($H_2O$), S-Basal buffer (SB), 25 mM sodium azide (azide) or 1 mM tetramisole (tet) in water, 500 mM glycerol in water, or 1.5×S-Basal buffer. Each dot represents the mean movement index over 3 min (see FIGS. 5 and 8), n=7-10 worms per condition. Vertical and error bars represent mean and standard deviation. Images represent typical movement under the conditions indicated by black arrows. Arrowheads indicate the edge of the hydrogel; animal movement can occur within this confined space (white arrows). Average range of motion over 3 minutes is indicated (FIG. 7). Scale bar equals 30 µm. Statistics were performed using ordinary 2-way ANOVA with Bonferroni's post hoc tests for pairwise comparisons: *P<0.05 is compared with the hydrogel control with SB and +P<0.05 is compared with the hydrogel cooling control with SB.

Figure 8:
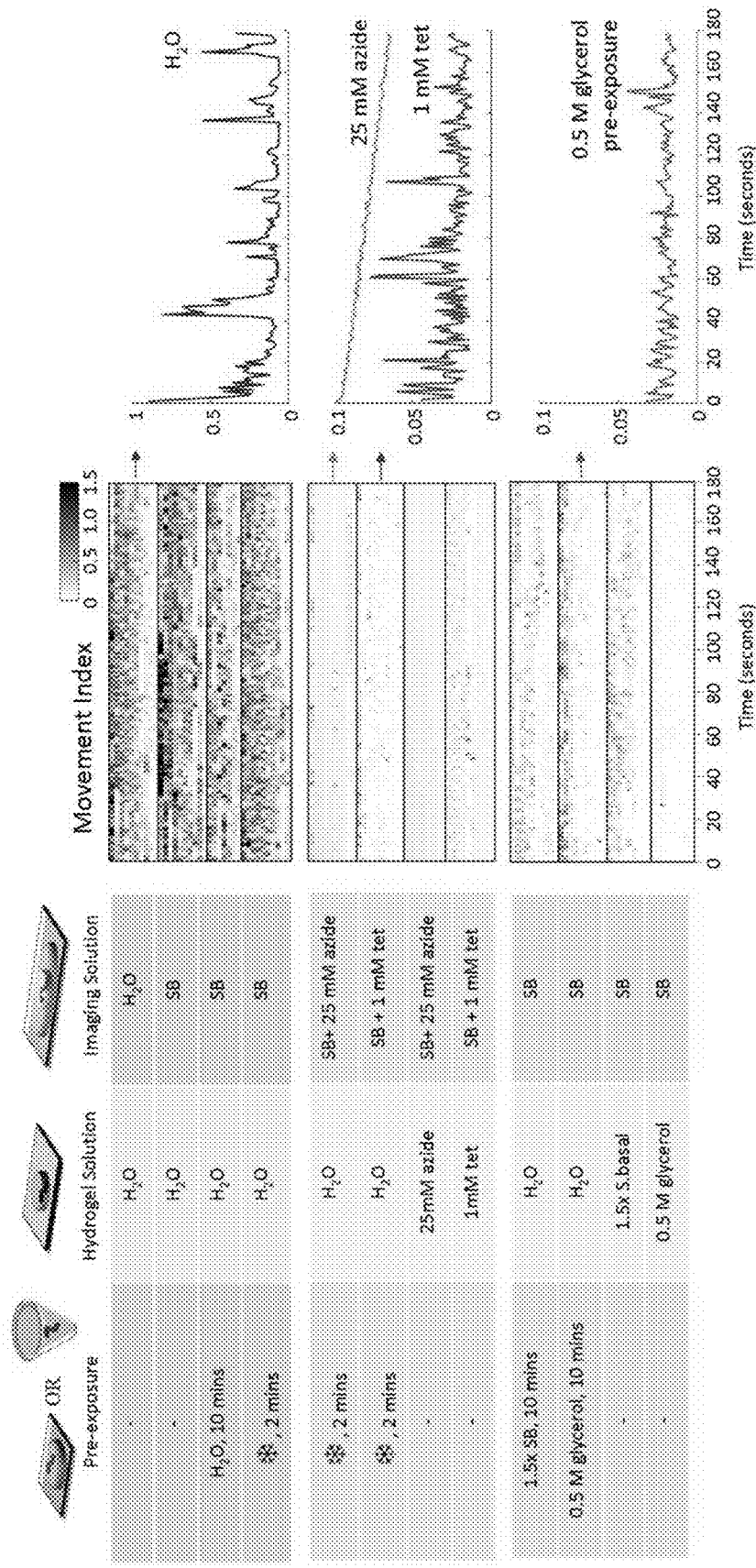
FIG. 8 shows the time course of movement over 3 min of animals embedded in different conditions before, during, and after hydrogel crosslinking.

Because encapsulated animals could push against the hydrogel and move or rotate slightly, we explored modifications that would reduce micron-scale movement for long-term high-resolution microscopy (FIG. 6). Micron-scale movement was quantified by tracking nuclei over 3 mins (FIG. 7) and by a Movement Index (M.I.) sensitive to changes in position, rotation, focus, and photobleaching (calculated as the relative pixel intensity difference across frames, FIG. 5). FIG. 7 shows displacement range over 3 minutes for animals embedded in different conditions before, during, and after hydrogel crosslinking. Pre-exposure to hypo- or hyper-osmotic solutions for 10 minutes, or cooling pretreatment (on ice or in a −20° C. freezer for 2 minutes) occurred in a droplet or microtube. Hydrogel solutions were prepared in water ($H_2O$), S-Basal buffer (SB), 25 mM sodium azide (azide) or 1 mM tetramisole (tet) in water, 500 mM glycerol in water, or 1.5×S-Basal buffer. (A) Mean displacement range over 3 min, from n=7-10 worms. Vertical line and error bars represent mean (standard deviation). (B) Comparisons between displacement and movement index are shown for 1 worm. (C) Correlation of movement index versus displacement, $R^2$=0.45. Statistics were performed using ordinary 2-way ANOVA with Bonferroni's post hoc tests for pairwise comparisons: *P<0.05 is compared with the hydrogel control with S-Basal solution. Movement of animals embedded in 20% PEG hydrogels averaged 39 µm over 3 minutes (16 µm-68 µm), with an average movement index (M.I.) of 0.33±0.21. Exposure to the paralytic reagents sodium azide or tetramisole significantly reduced micron-scale motion, both when applied during gelation and when applied transiently after encapsulation (18 µm, M.I. 0.07±0.01, and 19 µm, M.I. 0.06±0.02 respectively). Photobleaching observed when using sodium azide contributed a majority of the M.I. compared with tetramisole, as apparent in individual worm M.I. traces (FIG. 8). FIG. 8 shows buffer conditions before, during and after hydrogel crosslinking influence worm's variability in movement index during microscopy. Pre-exposure to hypo- or hyper-osmotic solutions for 10 minutes, or cooling pretreatment (* on ice or in a −20° C. freezer for 2 minutes) occurred in a droplet or microtube. Hydrogel solutions were prepared in water ($H_2O$), S-Basal buffer (SB), 25 mM sodium azide (azide) or 1 mM tetramisole (tet) in water, 500 mM glycerol in water, or 1.5×S-Basal buffer. Heat maps of movement index vs. time for the 3-minute duration of fluorescent imaging. In the middle panel, each line represents the movement index of an individual animal. On the right panel, the median movement index of each treatment group is represented.

Toward paralytic-free tight immobilization, we explored the ability for cooling temperatures or osmotic changes to reduce movement. Cooling to about 4° C. on ice temporarily immobilizes animals (Chung et al., 2008). However, while cooling stopped thrashing before crosslinking, movement after embedding remained similar to uncooled animals. Cooling also allowed animals to settle within the hydrogel droplet, positioning them parallel to the glass substrate for improved imaging.

Buffer osmolarity changes body size, shrinking animals in hyper-osmotic solutions over the course of minutes through the loss of water. We reasoned that animals placed in a hyper-osmotic solution before or during gelation would shrink, thereby reducing the encapsulation space and tightening their confinement upon return to normal osmolarity. Conversely, swelling animals before crosslinking in hypo-osmotic solutions could expand the hydrogel space, thereby providing more space for movement. Crosslinking the hydrogel in water (0 mOsm), then imaging in S-Basal buffer (280 mOsm), did not significantly increase movement (39 µm±17 µm range over 3 min, M.I. 0.45±0.24 compared with imaging in water (41±28 µm, M.I. 0.33±0.21). However, animals in a hyper-osmotic solution of 0.5 M glycerol (500 mOsm) and 1.5×S-Basal buffer (420 mOsm) for 10 minutes prior to or during crosslinking, then imaged in normal osmolarity S-Basal buffer, were well immobilized (8±7 µm range, M.I. 0.02±0.007 and 15±9 µm range, M.I. 0.07±0.05, respectively). These movement levels were comparable to immobilization by chemical paralytics.

Figure 9:
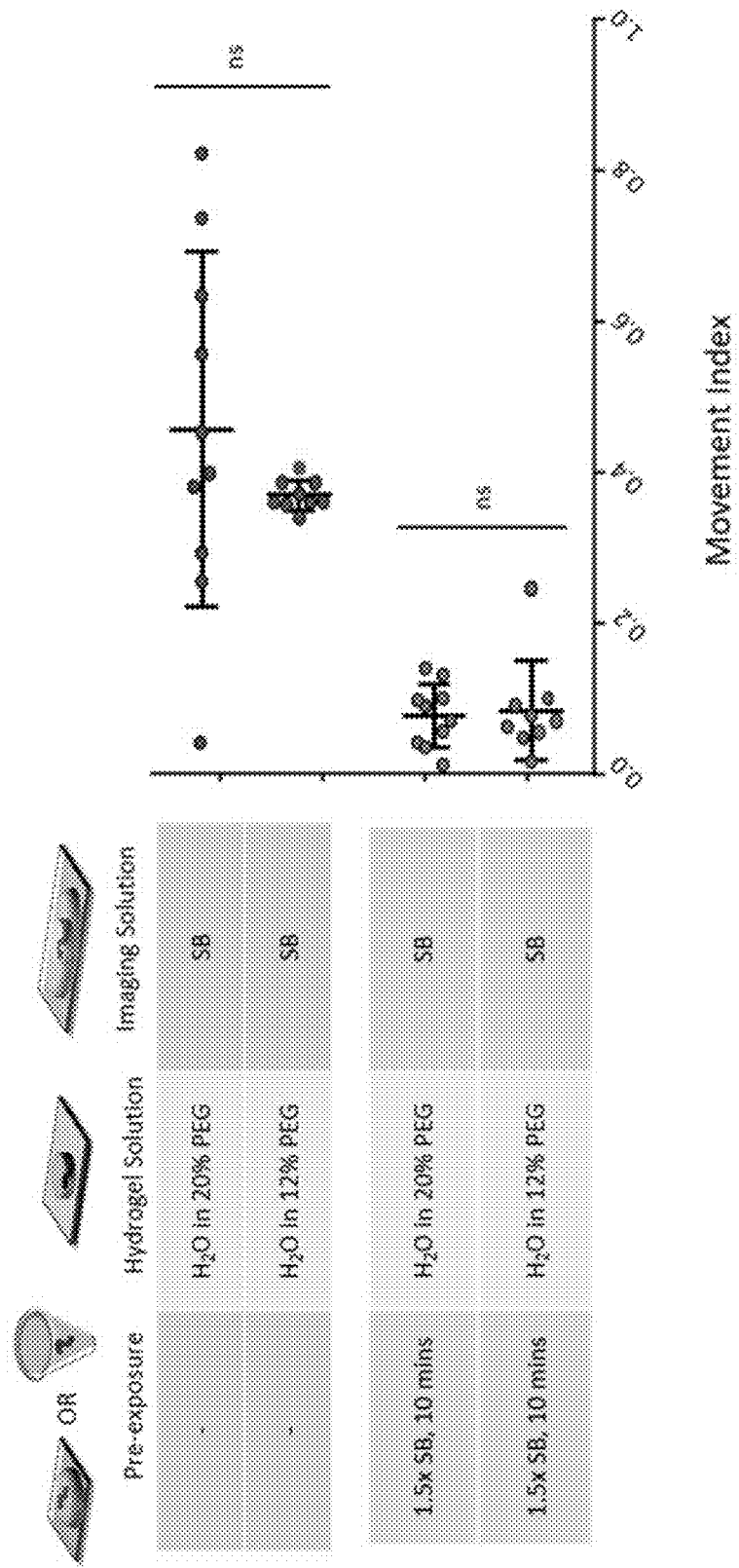
FIG. 9 shows similar movement of animals embedded in 20% and 12% PEG-DA hydrogels under control and hyperosmotic pre-exposure conditions.

Higher PEG-DA concentration reduced crosslinking time, as reported previously (Hockaday et al., 2012), and stiffer hydrogel disks were easier to handle than weaker ones. However, animal immobilization was as good in 12% gels as in stiffer 20% gels (FIG. 9). FIG. 9 shows movement of animals embedded in 20% and 12% PEG-DA hydrogels was similar under control and hyper-osmotic pre-exposure conditions (10 minutes pre-exposure to 1.5×S. Basal buffer in a droplet or microtube). Each dot plot represents the mean movement index over 3 min, from n=9-10 worms. Vertical and error bars represent mean (standard deviation). Statistics were performed using ordinary 2-way ANOVA with Bonferroni's post hoc tests for pairwise comparisons. This suggests that a concentration of 12% may be optimal for worm immobilization with higher diffusivity when gels needn't be moved, while higher concentrations may be preferred if gels need to be transferred by forceps.

Imaging Neural Activity in Encapsulated Adult Worms with Light Sheet Microscopy

Figure 10C:
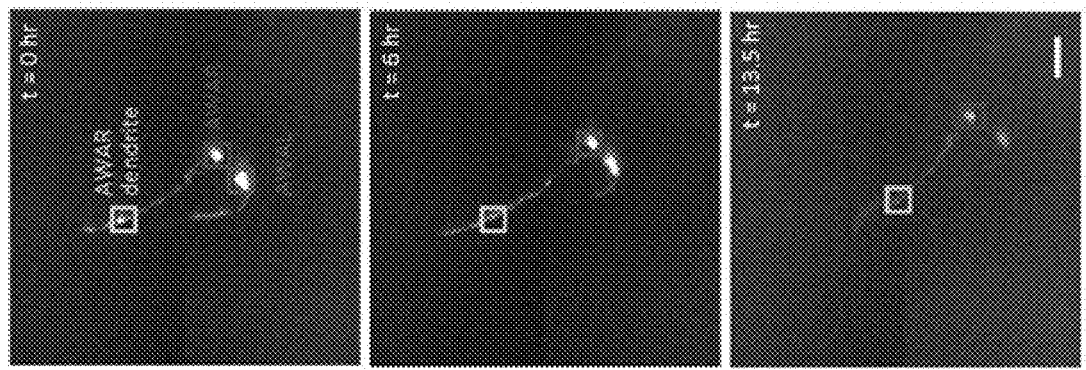
FIGS. 10A-10D illustrates long-term imaging of red light-activated responses in AWA neurons expressing Chrimson and GCaMP2.2b using diSPIM.
Figure 10A:
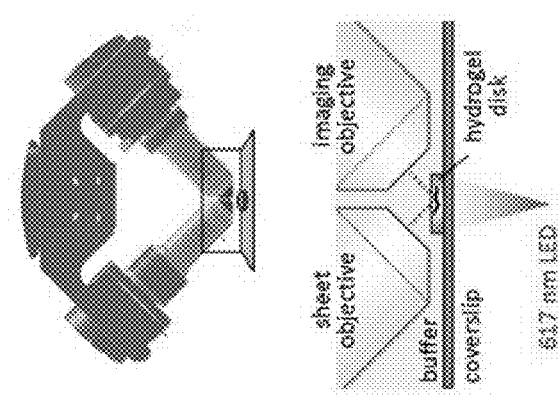
Figure 10B:
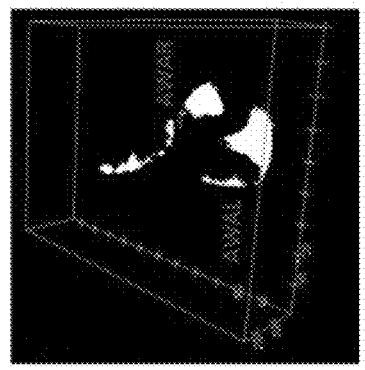
Figure 10D:
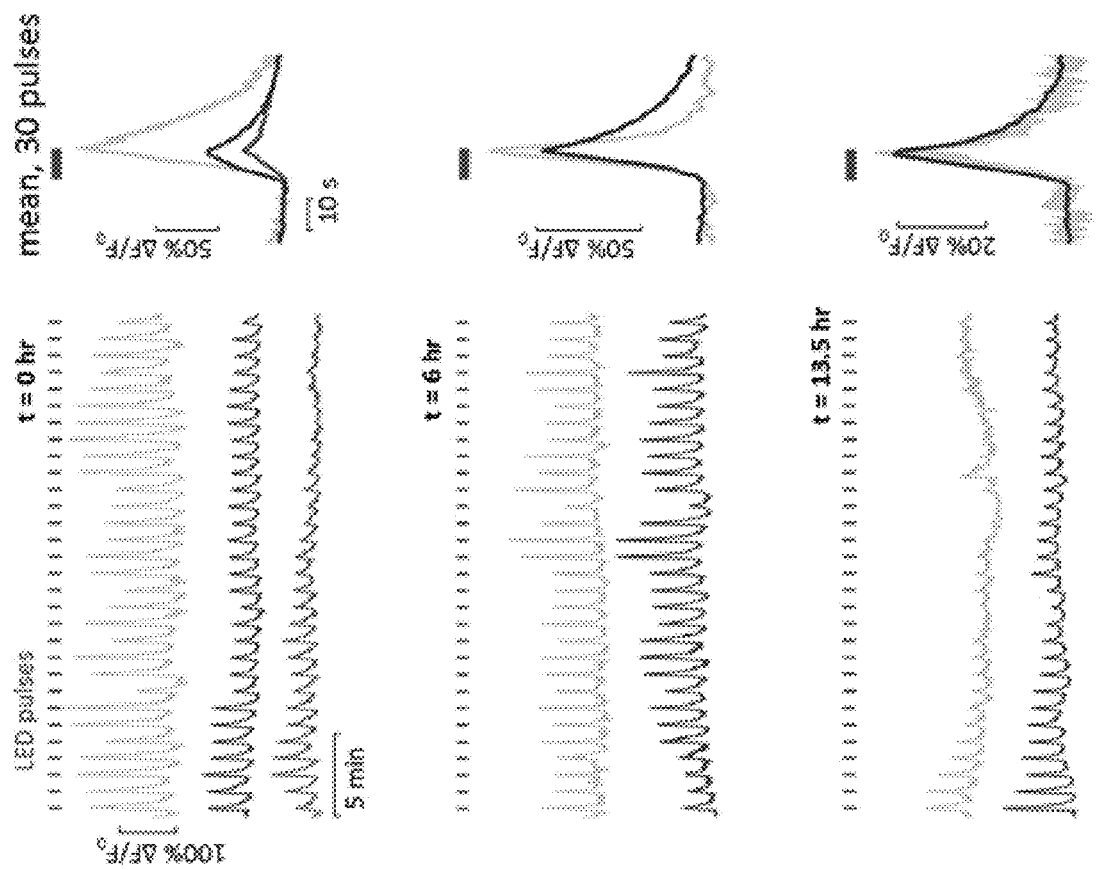

FIG. 10A-FIG. 10D illustrate long-term imaging of red light-activated AWA neurons expressing Chrimson and GCaMP2.2b using diSPIM. FIG. 10A shows a schematic of diSPIM objectives, hydrogel, and red light exposure. FIG. 10B shows a three dimensional volumetric view of AWA neurons. FIG. 10C shows a maximum intensity projection of highlighting ROIs of AWAL and AWR cell bodies and AWAR dendrite. Scale bar, 20 μm. FIG. 10D shows a time-lapse recording of GCaMP signal in each ROI at t=0 hr, 6 hr, and 13.5 hr time points. LED was pulsed for 10 seconds, once per minute, for 1 hour; 30 mins are shown for clarity. At right, mean $\Delta F/F_0$ is calculated for the 30 stimulation pulses indicated at left, with shading indicating SEM, and bars indicating 10-s red light exposure.

Hydrogels are nearly index-matched with water, therefore suitable for light sheet microscopy. We used PEG hydrogel immobilization to image young adult *C. elegans* for up to 14 hours without chemical paralytics. Worms expressing the Chrimson channel and GCaMP calcium reporter in the AWA neuron pair were imaged for three 1 hour trials over 14 hours, stimulated with 10-s pulses of red light every minute. Responses were reliably observed in the soma and neurites of both AWAL and AWAR neurons after embedding, and continued strongly in AWAR after 6 h and 13.5 h at room temperature (FIG. 10A-FIG. 10D). Responses in AWAL declined over the first hour, and while present at the beginning of 6 h and 13.5 h trials, declined further over time. AWAR response magnitude declined about 2-fold over 14 hrs in the cell body and 5-fold in neurites.

Encapsulation and Imaging of Squid Hatchlings

Figure 11C:
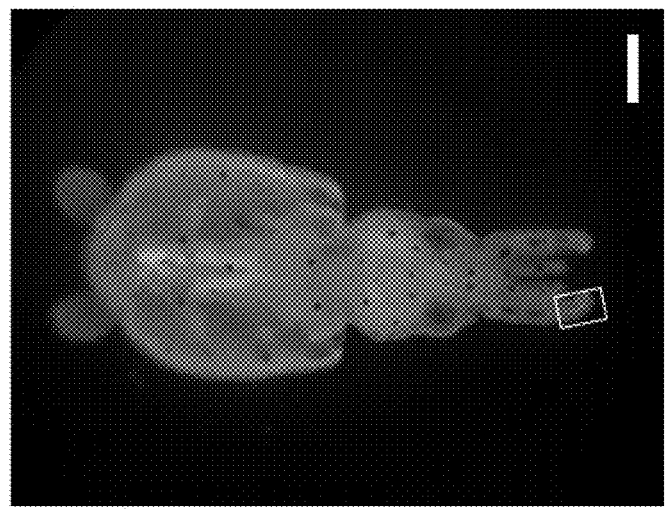
FIGS. 11A-11D show imaged encapsulated pygmy squid using diSPIM light sheet microscopy.
Figure 11B:
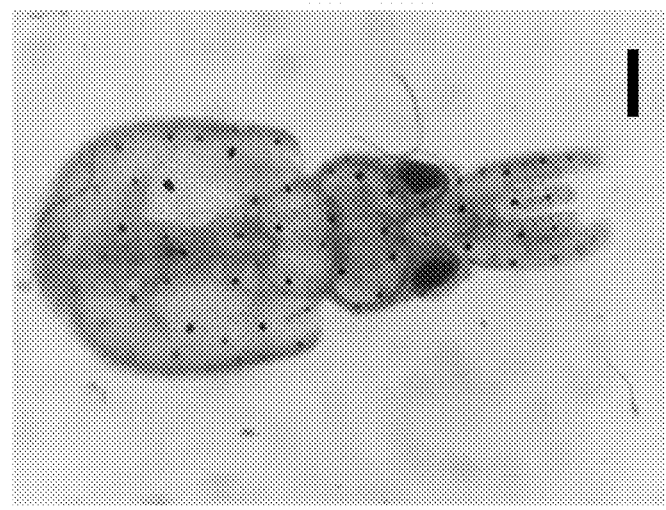
Figure 11A:
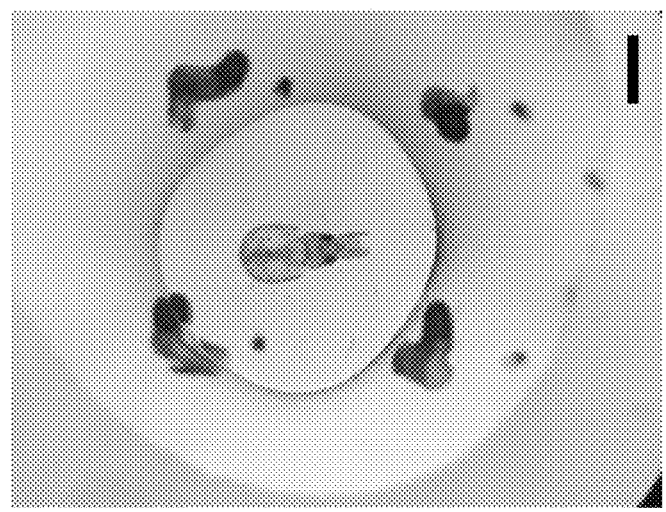
Figure 11D:
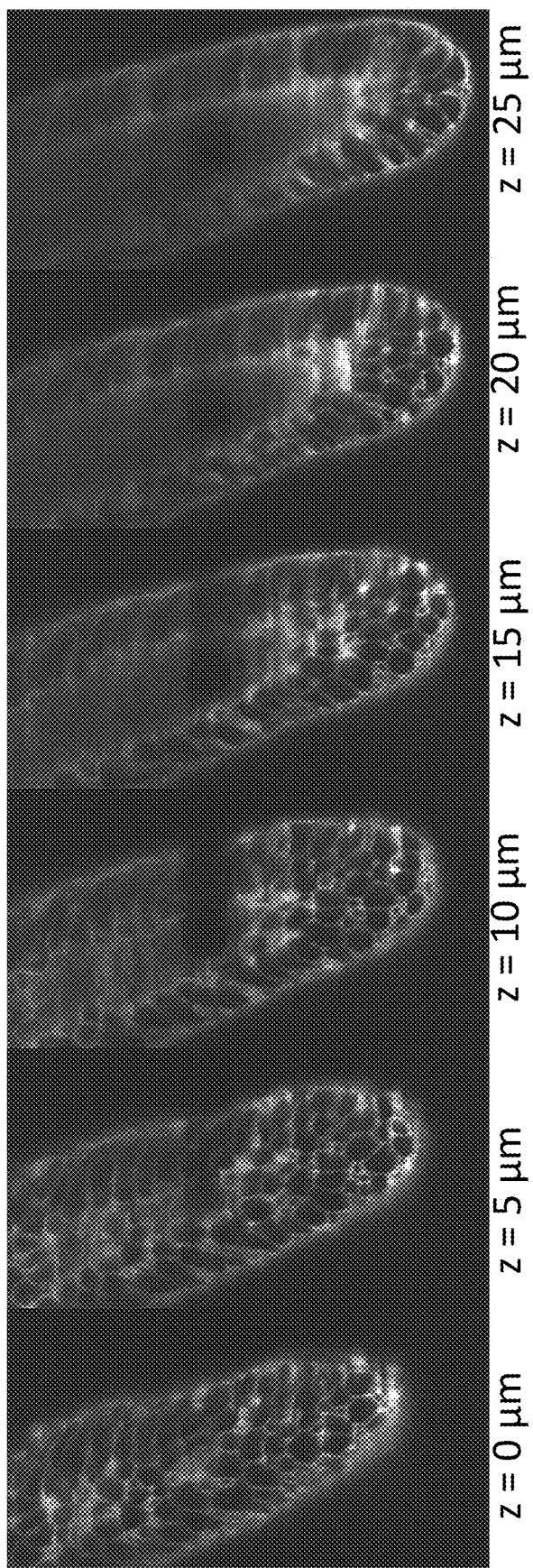

Soft mounting methods are especially important for flexible specimens, such as marine organisms. Three-day old living pygmy squid hatchlings were encapsulated in 1.2 mm thick, 4 mm diameter 16% PEG hydrogel disks under anaesthesia and transferred them to sea water for recovery (FIG. 11A-FIG. 11D After several minutes, hearts were beating and chromatophores actively opened and closed, indicating recovery of muscular behavior in internal structures. External structures in contact with the hydrogel, including arms, fins, and mantle, were immobilized. The hatchlings were viewed in brightfield (FIGS. 11A and 11B). Prior to encapsulation, squid were stained with 1 BODIPY C3 succinimidyl ester dye to generally label cell boundaries throughout the organism, as viewed on a fluorescent dissecting microscope (FIG. 11C). A volumetric stack was obtained using the diSPIM light sheet microscope through the tip of one arm of the squid—FIG. 11D shows raw light sheet image slices of one squid arm indicated in FIG. 11C (box) at 5 μm increments. Scale bars: 1 mm (a), 250 μm (b,c), 50 μm (d). Sharp cellular borders and slice alignment indicate minimal movement during image capture.

Encapsulation and Imaging for High-Content Screening

Figure 12E:
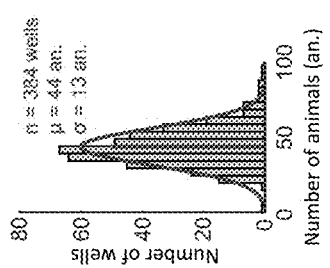

FIGS. 12A-12F show an exemplary method overview for automated long-term high-content screening of functional cellular activity in *C. elegans* enabled by gel immobilization, optical stimulation, and recording. FIG. 12A shows the general procedure for filling and preparing a 384 well plate to use in the automated experiment. Animals are first age synchronized on plates for a period of time, for example 12 hours (step 60), and grow for a period of time, for example 48 hours (step 62), and ~15,000 are resuspended in 10% PEGDA gel at, for example ~4 animals/μL concentration or ~5 animals/μL concentration (step 64). Each well of a 384 well plate is filled with 10 μL of liquid and ~40 animals/well (step 66), for example, using a liquid handling robot. Immobilization and settling of the animals can occur by cooling, for example, for approximately 10 minutes (step 68). For example, the filled well plate is placed at −20 C to induce immobilization, then crosslinked at 308 nm for 45 s (step 70). A custom program was written to deposit 404, of solution to each well containing drugs or any liquid of interest, or can be customized to add >40 μL of solution to each well containing different compounds. A transfer to a drug library is done in step 72, and an automated screen is done in step 74. FIG. 12B shows the custom microscope hardware and configuration for optical recording and stimulation of individual wells containing animals. Zoom-out shows one well out of 384 that contains 20% gel with animals (10 and 80% compound (40 FIG. 12C shows an illustration of animals used for functional screening. Zoom-out shows excitation and emission wavelengths corresponding to b. Animals co-express integrated versions of Chrimson and GCaMP in the AWA chemosensory neuron. FIG. 12D shows a full-resolution image stitch of a 384 well plate after preparation described in a. Magnified zoom-out shows ~40 animals in a single well with excitation wavelengths (arrows) pointing at the AWA neuron of one animal. FIG. 12E shows a histogram distribution and normal fit of animals per well in a prepared 384 well plate shown in FIG. 12D. Average number of animals in each well of a 384 well plate is 44±13 animals. FIG. 12F shows average $\Delta F/F_0$ calcium response trace of 41 wild-type animals described in FIG. 12C immobilized in one well, as shown in FIG. 12D. Shading 76 in FIG. 12F indicates light pulse stimulus. Shading represents SEM. Individual animal traces are represented on each line of the heat map below sorted in descending order by peak $\Delta F/F_0$ response during stimulation.

Figures 13A, 13B:
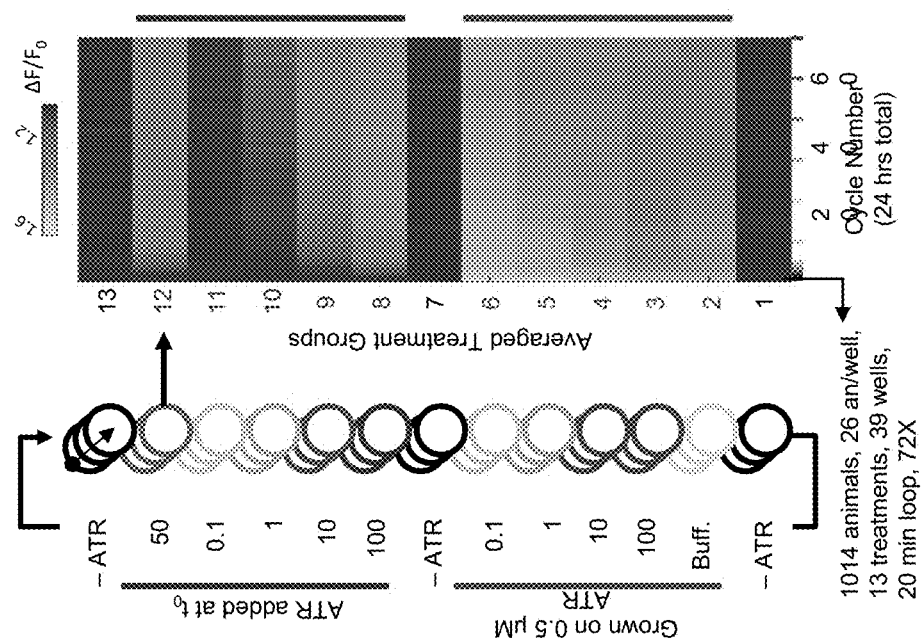

FIGS. 13A-13G shows an automated assessment of a 24-hour time course and ATR dose response threshold for optogenetically-evoked calcium responses in *C. elegans*. FIG. 13A shows multiwell plate schematic representing 39 independent wells, with 13 treatments and 3 technical well replicates of each condition (stacked wells). Three negative controls (−ATR) and two ATR treatment conditions across three orders of magnitude are indicated by color and labeled with treatment concentration and conditions. One stimulus per well was repeated every 20 min, 72 times lasting 24 hours total. FIG. 13B shows a heat map representation of average $\Delta F/F_0$ peak responses from all three row treatments corresponding to the schematic and labels in a, for 72 cycles (24 hrs total) of repeated excitation (every 20 min). The heat map represents 936 average $\Delta F/F_0$ peak data points derived from at least 73,000 total individual peak $\Delta F/F_0$ data points. FIG. 13C shows average $\Delta F/F_0$ calcium response traces for all treatments corresponding to rows 2-6 in FIG. 13A and FIG. 13B, organized horizontally. The first 6 cycles (2 hours) and every 2-4 hours thereafter as indicated by the color bar (right) and x-axis in FIG. 13B. FIG. 13D shows the same layout and data representation as described in FIG. 13C, but corresponding to rows 7-12 in FIG. 13A and FIG. 13B. FIG. 13E shows quantification of average peak $\Delta F/F_0$ calcium responses per condition across all cycles (24 hours total). Line and shading colors represent either plate (orange) or well (blue) treatment conditions, while ATR negative controls are in black (flat curves). Trace shading represents SEM. Red shaded bars and x-axis color bar represent sampled trace time points as described in FIG. 13C. FIG. 13F shows a bar plot of relative average peak $\Delta F/F_0$ calcium responses per condition to row 1 (−ATR), consistent with well outline colors described and shown in a, for the 24 hour ($72^{nd}$) time point (arrow from FIG. 13E to FIG. 13F, and last red shading duration). Symbols represent significance after a one-way ANOVA with Bonferroni's method of correction for multiple comparisons ( $p<0.01$, * $p<0.001$). Error bars represent SEM. FIG. 13G shows average $\Delta F/F_0$ calcium response traces for the last cycle ($72^{nd}$) at 24 hours for the well treatment condition at 100 μM, 1 μM, and 0.1 μM concentrations as labeled, corresponding to the darkest red traces in FIG. 13D, bar plot colors in FIG. 13F, and row 8, 10, and 11 in FIG. 13A, and FIG. 13B. Shading represents SEM.

Figure 14A:
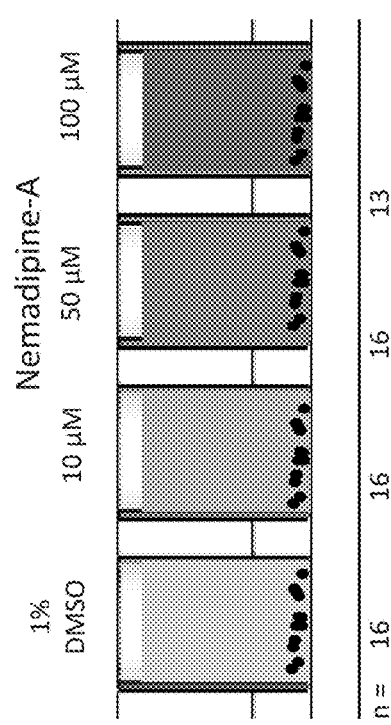
Figure 14B:
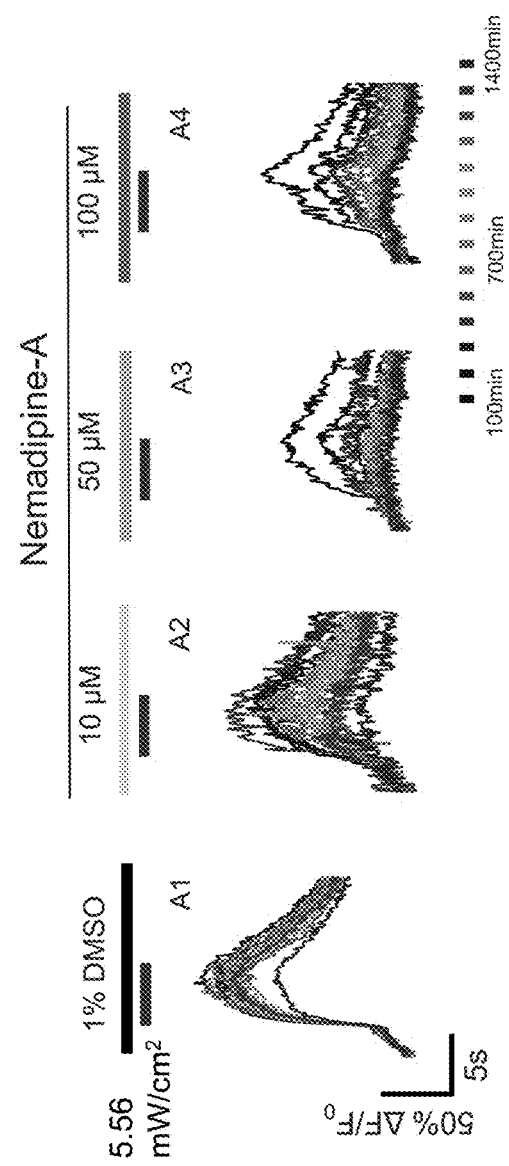

FIG. 14A-FIG. 14E show how the calcium channel blocker Nemadipine-A has time and dose dependent effects on AWA activity. FIG. 14A shows a side-view of the experimental conditions for 4 wells being tested, the first having 1% DMSO solvent control, the next three increasing concentrations of Nemadipine-A from 10, 50, 100 uM (left to right). FIG. 14B shows the change in fluorescent activity over time with time course results from animals in each well showing the drug or control condition above and pulse timing as the red bar. The time course was set to stimulate each well every 10 min for 24 hours, showing the first 10 pulses, then only every 100 min colormetrically from violet to red with traces overlaid. The overall trend from left to right (control to highest drug concentration) is a reduction in peak response, representing the activity of the calcium channel blocking drug with dose dependence. FIG. 14C shows the quantification of peaks for each condition over the same time course described in FIG. 14B, error bars represent SEM and colors represent well solution condition. FIG. 14D shows that the change in fluorescent calcium activity responses depend on the voltage-gated calcium channel EGL-19. Animals were prepped as previously described into 3 individual wells and stimulated once per well. FIG. 14E shows an image-stitch representation of the scalability of this experiment for future testing, with a full-resolution zoom-in of two wells with ~40 age synchronized animals per well. For example, the experiment can scale up to a 384 well plate. In some embodiments, ~95% of these wells contained sufficient animals for recording.

Figure 15A:
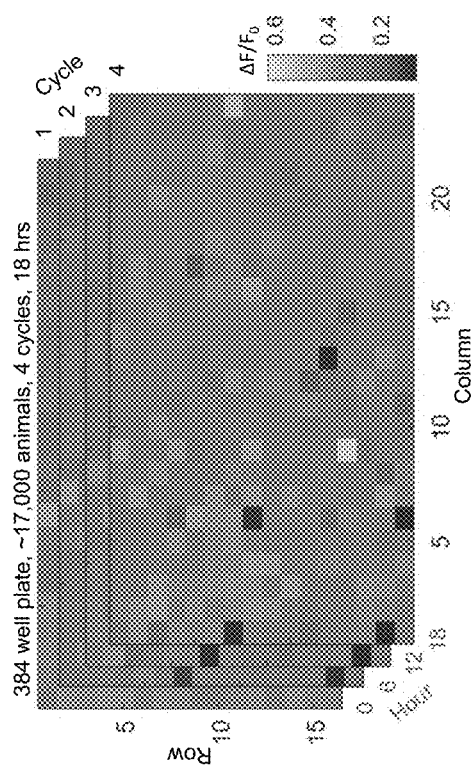
Figures 15B, 15C:
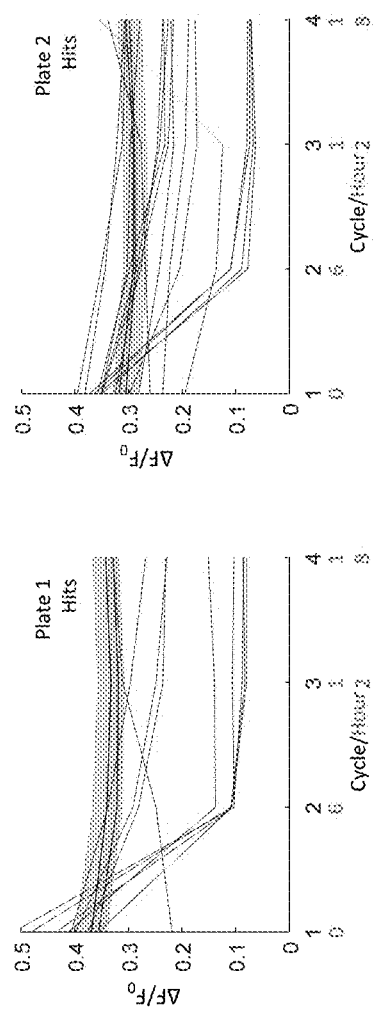
Figures 15D, 15E:
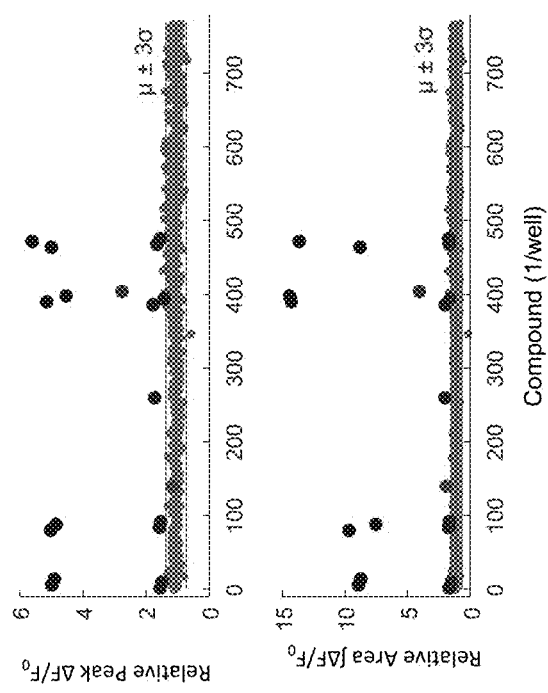

FIGS. 15A-15K shows the identification of optogenically-evoked calcium activity suppressors using the automated long-term high-content functional screening method. FIG. 15A shows four stacked heat maps representing average peak $\Delta F/F_0$ calcium responses for ~44 genetically identical animals per well of a 384 well plate at 0 hr, 6 hr, 12 hr, and 18 hr (cycle 1, 2, 3 and 4, respectively) time points. Each well contains a different compound, except for controls. FIG. 15B shows average peak $\Delta F/F_0$ calcium responses for each well of the first plate screened for all cycles, grouped by either buffer controls (black line, gray shading represents SEM) or drugs (thicker red line, red shading represents SEM). Individual thin red lines represent compounds with relative peak $\Delta F/F_0$ calcium responses beyond three standard deviations from the average peak $\Delta F/F_0$ calcium response of buffer controls. FIG. 15C shows the same description as in b for a second independent plate screen. FIG. 15D shows a scatter plot of average relative peak $\Delta F/F_0$ calcium response per well, representing fold change (comparing cycle 4 to 1). Nemadipine-A controls are colored purple (100 µM) or dark blue (10 while other positive hits are colored green (felodipine) or dark orange (ivermectin), both at 10 µM. Red lines represent the mean±3 standard deviations. FIG. 15E (the same description as in d) shows average fold change in area from integrated $\Delta F/F_0$ calcium responses. Dot colors and red lines are consistent with d. The red dot highlights a compound with significant fold change in area, not identified by relative peak quantification in d, but due to a noise artifact. FIG. 15F shows overlaid average $\Delta F/F_0$ calcium response traces for all four time points from darker to lighter colored shading (0 hr-18 hr, respectively) of 1% DMSO. Trace shading colors correspond to dots in d and represents SEM. FIG. 15G shows overlaid average $\Delta F/F_0$ calcium response traces as in f for 10 µM nemadipine-A. FIG. 15H for 10 µM felodipine. FIG. 15I for 100 µM nemadipine-A. FIG. 15J for 10 µM ivermectin. FIG. 15K shows a bar plot of normalized average peak $\Delta F/F_0$ calcium responses to the first cycle for all cycles, with colors corresponding to traces in FIG. 15F. Symbols represent significance after a two-way repeated measures mixed ANOVA with Bonferroni's method of correction for multiple comparisons (** $p<0.01$). Error bars represent SEM.

Figure 16C:
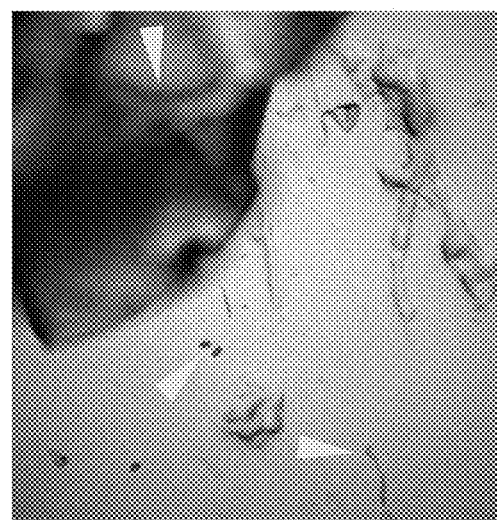
FIGS. 16A-16C shows recovery of animals from a selected 10% PEGDA crosslinked gel in a well of the 384 well plate after greater than 12 hrs for propagation of previously treated animals.
Figure 16B:
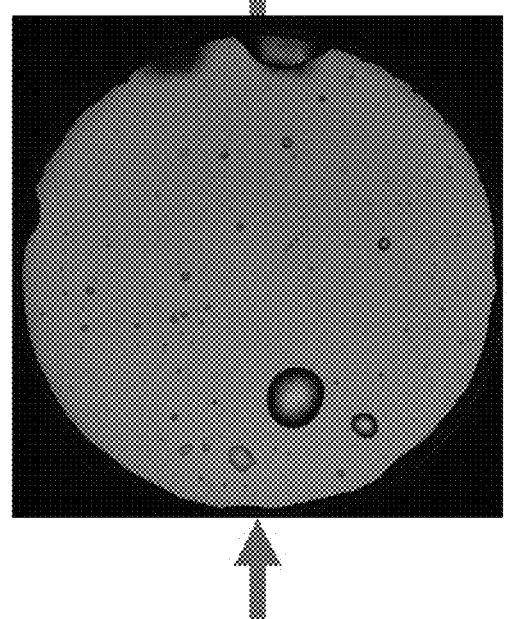
Figure 16A:
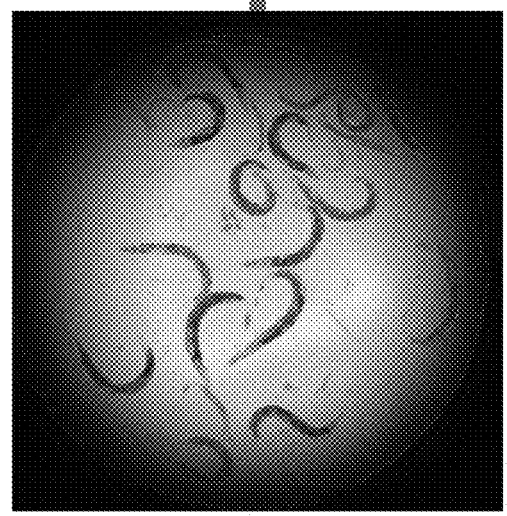

FIG. 16A-FIG. 16C shows recovery of animals from a selected 10% PEGDA crosslinked gel in a well of the 384 well plate after >12 hrs for propagation of previously treated animals. In some instances, it is desirable to propagate animals with selected phenotypes following screening, such as for a secondary screen or examination of behavioral effects. C. elegans that were embedded in 10% PEGDA of a 384 well plate are recoverable by transferring the gel to an agar plate and breaking the gel with a pipette tip.

Figure 17A:
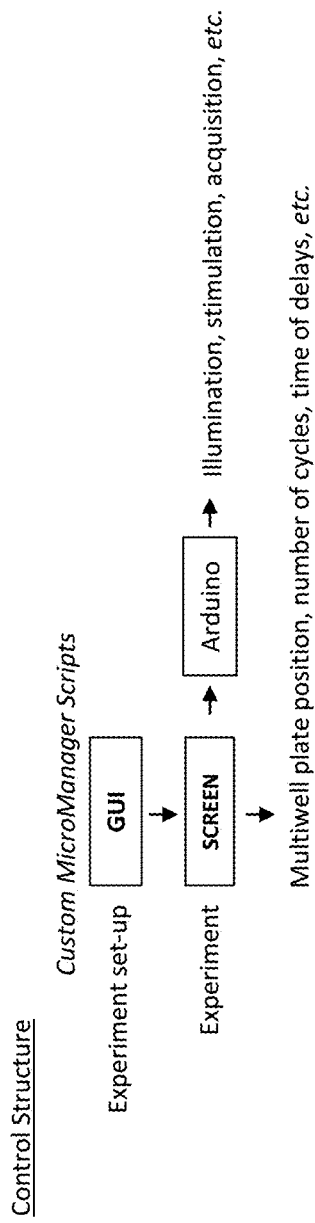
FIGS. 17A-17F shows a software suite of control scripts for user-defined automated experimental control.
Figure 17B:
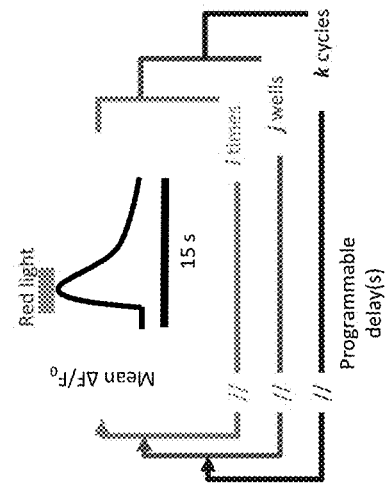
Figure 17D:
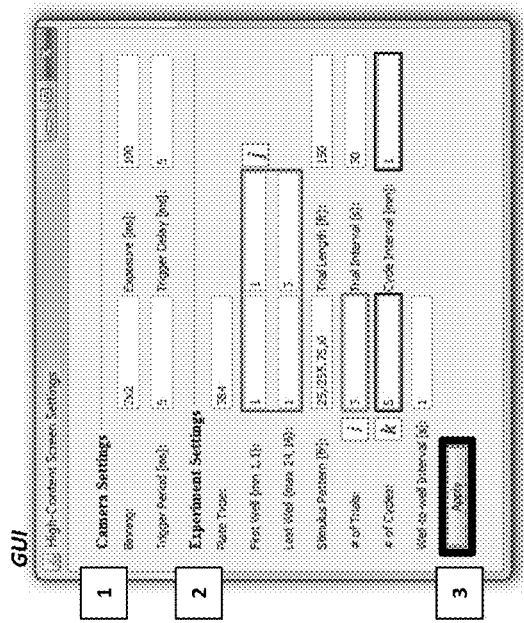
Figure 17C:
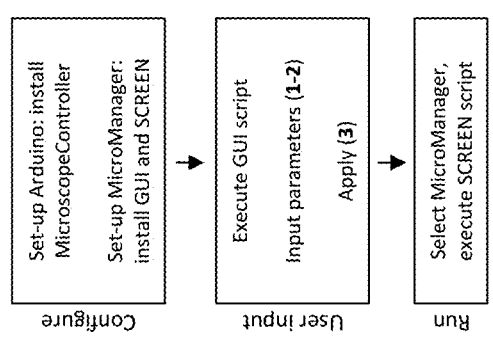
Figures 17E, 17F:
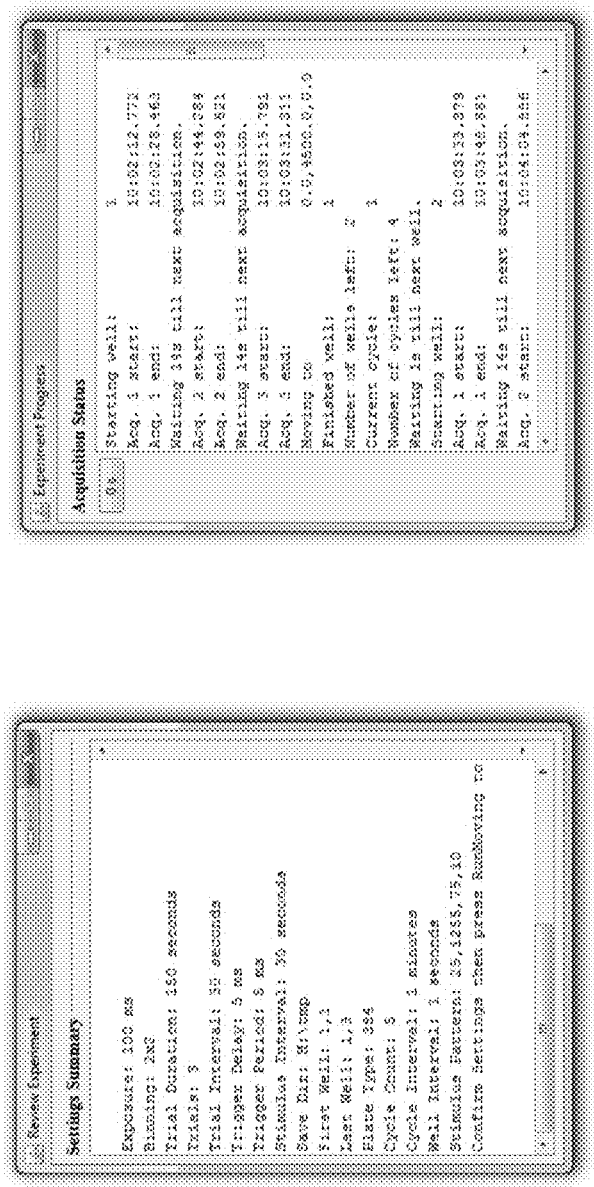

FIGS. 17A-17F shows the custom suite of MicroManager control scripts for user-defined automated experimental control. FIG. 17A shows a flow diagram outlining the control structure for experimental automation. Custom MicroManager scripts were developed for user input of experimental settings (GUI) before each execution (SCREEN). An Arduino microcontroller synchronizes timing of pulse stimulation and illumination, coordinated with camera execution, file saving, timing, and MicroManager x-y plate position control. FIG. 17B describes that each experiment requires user input of stimulus pulse length (red light duration), recording duration (15 s shown), number of repeat stimuli (i), wells to repeat (j), and well cycles to complete (k), each with programmable delay options. FIG. 17C shows the set-up sequence for first-time installation and execution of software. The first box shows requirements for software configuration, the second box outlines required steps for user input, and the third box describes experimental execution. FIG. 17D shows the High-Content Screen Settings GUI showing user determined (1) Camera Settings, (2) Experiment Settings, and the settings (3) Apply button. Colors correspond to control settings shown in FIG. 17B. FIG. 17E shows the Review Experiment window with a preview of applied user determined variables, which is saved to the local drive experiment folder for direct experimental repeats and logged settings history. FIG. 17F shows the Experiment Progress window that updates in real time throughout the experiment with current experimental parameters, like current plate position, cycle, well, etc. This metadata file is also saved to the experiment folder for logged history.

FIG. 18A is a schematic showing 20-40 animals that were picked into a PCR tube containing 10 uL of 4.8% LF 10/60 alginate in $H_2O$ and transferred per well of a 384 well plate. FIG. 18A illustrates a single well in the 384 well plate, and the process of crosslinking occurring in that well. 10 uL of 102 mM $CaCl_2$) was added to the edge of the well, then image capture resumed during ionic gelation and gradual worm immobilization. FIG. 18B shows dissolution of the gel at three different time by the addition of the calcium chelator sodium citrate.

FIGS. 19A-19E show an exemplary embodiment of an immobilization of C. elegans in one well of a 384 well plate using the hydrogel, and successful recovery of embedded animals to standard NGM plates. FIG. 19A shows the first frame of a 30 second bright-field video demonstrating different z-depth positions of ~40 animals in the liquid phase of the hydrogel before the crosslinking of the hydrogel, which allows the organisms to thrash in the hydrogel. A frame 5 seconds after the first, demonstrating relative animal movement to the overlaid grid lines to the time point above. Scale bar, 500 µm. FIG. 19B shows the first frame of a 30 second bright-field video demonstrating uniform z-depth position of the same animals at the bottom of the well plate after settling and crosslinking. A frame 5 seconds after the first, demonstrating no relative animal movement to the overlaid grid lines to the time point above (scale bar, 700 µm). FIG. 19C shows a fluorescent (for example, 470 nm) excitation image, shows fluorescent animal tails and AWA neurons (scale bar, 700 µm). In FIG. 19C, the organisms are immobilized. FIG. 19D shows a low magnification bright-filed image demonstrating successful removal of the gel disk from FIG. 19B or FIG. 19C on a standard NGM plate with OP50 E. coli. The arrows represent animals that escaped and recovered from the gel disk, with a scale bar of 1.4 mm. FIG. 19E shows an image similar to FIG. 19D at a later time point shows a dissected, open gel to assist animals in escaping the hydrogel for propagation and follow-up assays. The arrows show that several more animals were able to escape freely, with a scale bar of 1.4 mm.

Figure 20A:
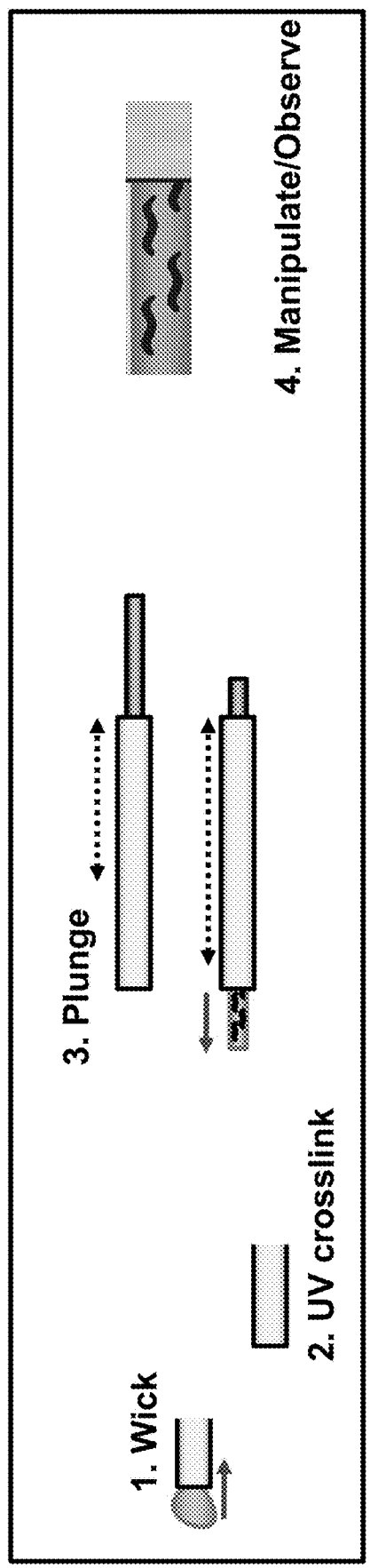
FIGS. 20A-20D illustrates an exemplary embodiment for hydrogel crosslinking of an organism contained within a microcapillary for light-sheet imaging.
Figure 20D:
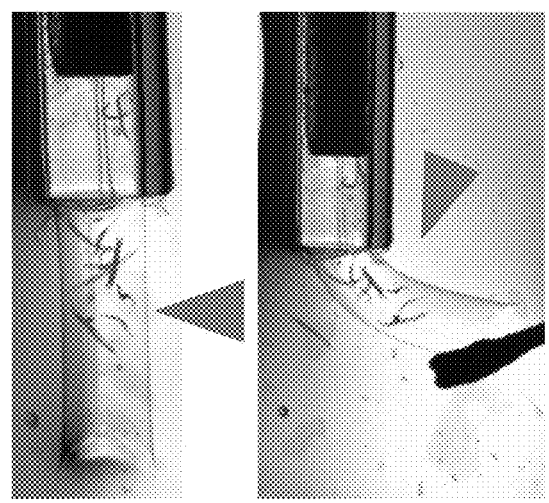
Figure 20C:
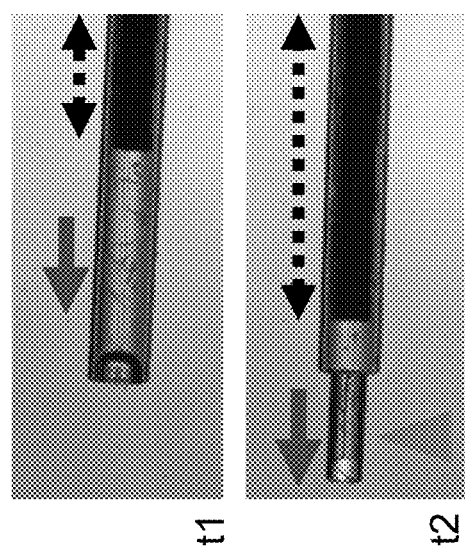
Figure 20B:
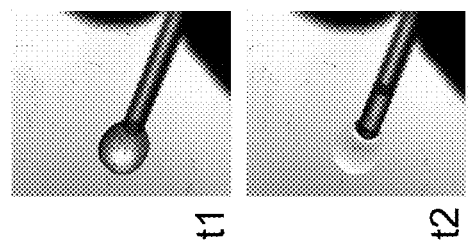

FIGS. 20A-20D demonstrates an exemplary procedure for hydrogel crosslinking of C. elegans contained within a microcapillary for light-sheet imaging. FIG. 20A shows a procedure schematic overview. FIG. 20B shows wicking of the hydrogel solution with worms into the microcapillary by capillary action forces at two time points before (t1) and seconds after (t2). FIG. 20C demonstrates plunging of the crosslinked hydrogel with worms now embedded. The blue arrow shows the gel extrusion displaced from within the glass microcapillary due to plunging forces (purple arrows). FIG. 20D shows mechanical bending of the hydrogel extrusion, with blue arrows pointing to the deflected hydrogel.

Figure 21C:
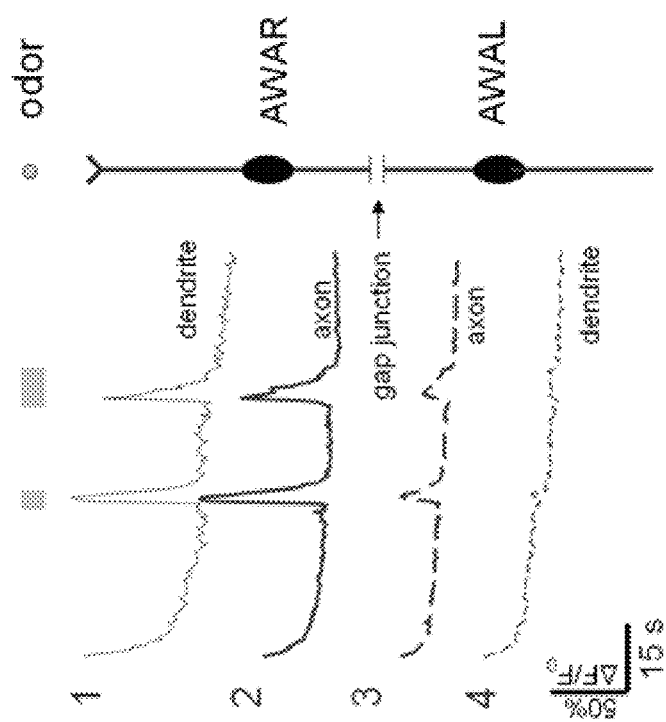
FIGS. 21A-21C demonstrate rapid presentation of chemical pulses to hydrogel-embedded organisms.
Figure 21A:
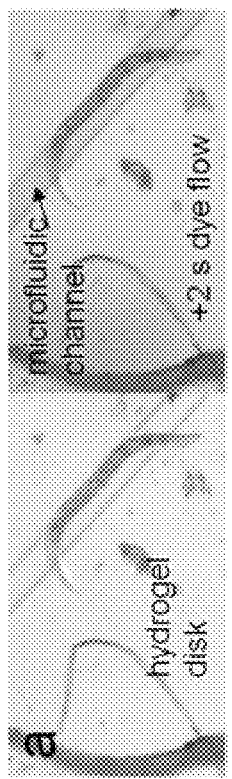
Figure 21B:
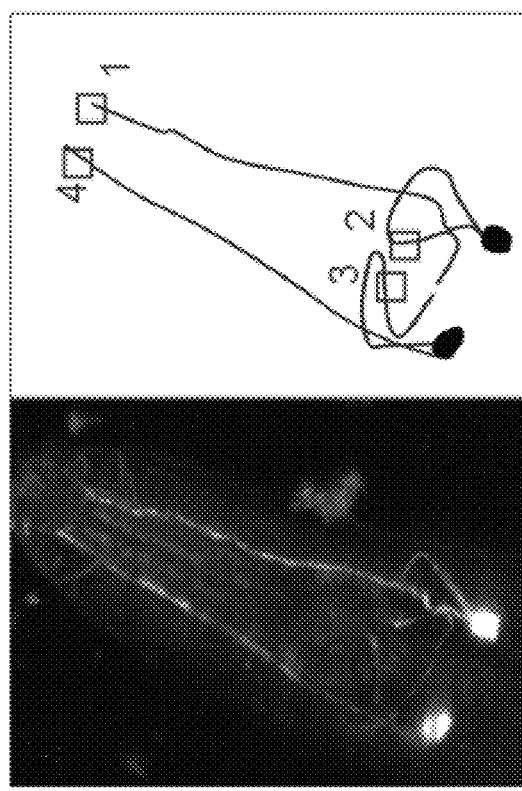

FIGS. 21A-21C demonstrate rapid presentation of chemical pulses to hydrogel-embedded organisms, such as C. elegans. FIG. 21A shows an example of microfluidic presentation of a chemical dye to stimulate PEG hydrogel-encapsulated organisms with precise timing. Wild-type C. elegans expressing GCaMP in the AWA sensory neuron pair were encapsulated in a hydrogel disk above a 100 µm wide microfluidic channel. External tubing connections and valves delivered 1, 5, or 10 second long pulses of chemical flow beneath the hydrogel disk. Small molecule chemicals (MW<500 Da) diffuse rapidly through the hydrogel, typically in under 1 second, to reach the encapsulated organism(s). FIG. 21B shows a maximum-projection light sheet image (using a diSPIM microscope, 40 slices per volume) and diagram of the AWA sensory neuron pair. FIG. 21C shows relative integrated fluorescence in four locations following diacetyl odor stimulation for 5-s and 10-s. In this example, diacetyl stimulated one of the two neurons (near location 1), whose signal transmitted partially across a gap junction at the axons (locations 2 and 3).

Figure 22C:
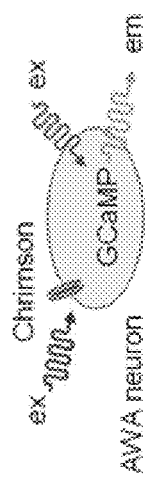
FIGS. 22A-22D demonstrate different approaches for simultaneous optogenetic neural activation and neural activity readout, using spectrally-segregated reagent pairs.
Figure 22D:
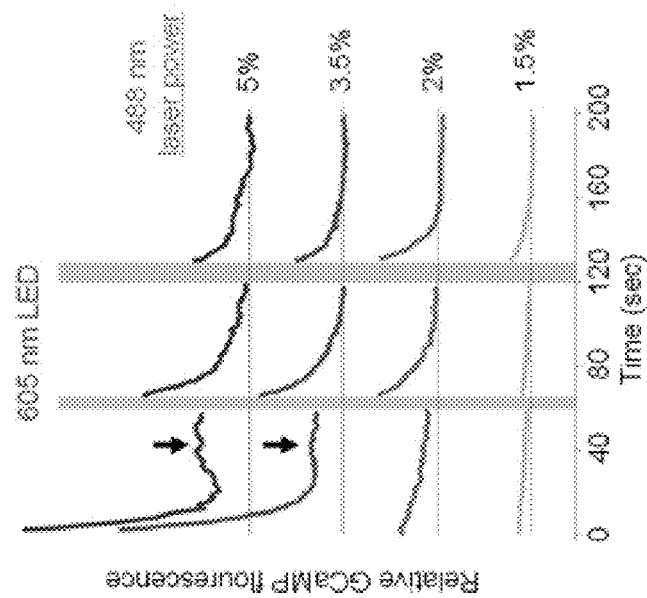
Figure 22A:
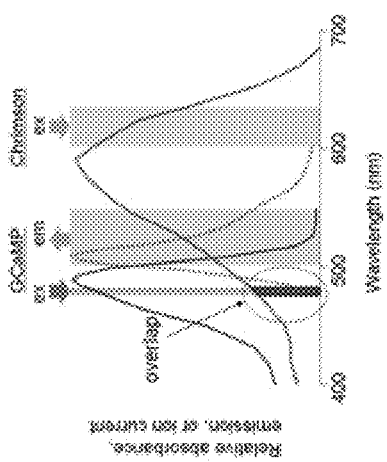
Figure 22B:
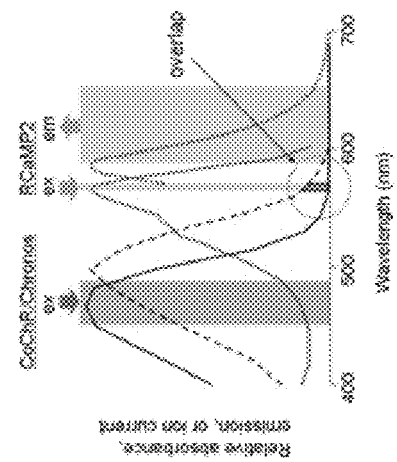

FIGS. 22A-22D demonstrate different approaches for simultaneous optogenetic neural activation and neural activity readout, using spectrally-segregated reagent pairs. FIG. 22A shows the excitation and emission spectra of Chrimson (red) for neural stimulation and GCaMP (green) for readout of neural activity via intracellular calcium. FIG. 22B shows similar spectra for CoChR or Chronos (blue) for neural stimulation and RCaMP2 (red) for neural activity readout. Excitation (ex) and emission (em) spectra highlight some overlap between excitation wavelength of the calcium reporter and of the light-activated ion channel. FIG. 22C shows an experimental setup in which both excitation and readout reagents are expressed in the same neuron (AWA). FIG. 22D shows that by minimizing the excitation light for neural readout, undesired neural activation can be reduced. Shown are diSPIM recordings of a sensory neuron co-expressing GCaMP2.2b and Chrimson activated by red light. Arrows indicate the "observer effect" due to premature activation by intense excitation light.

Figure 23C:
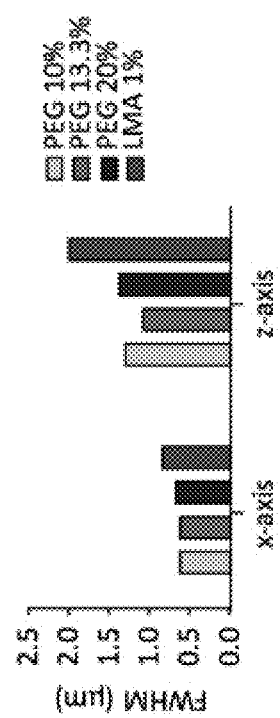
Figure 23D:
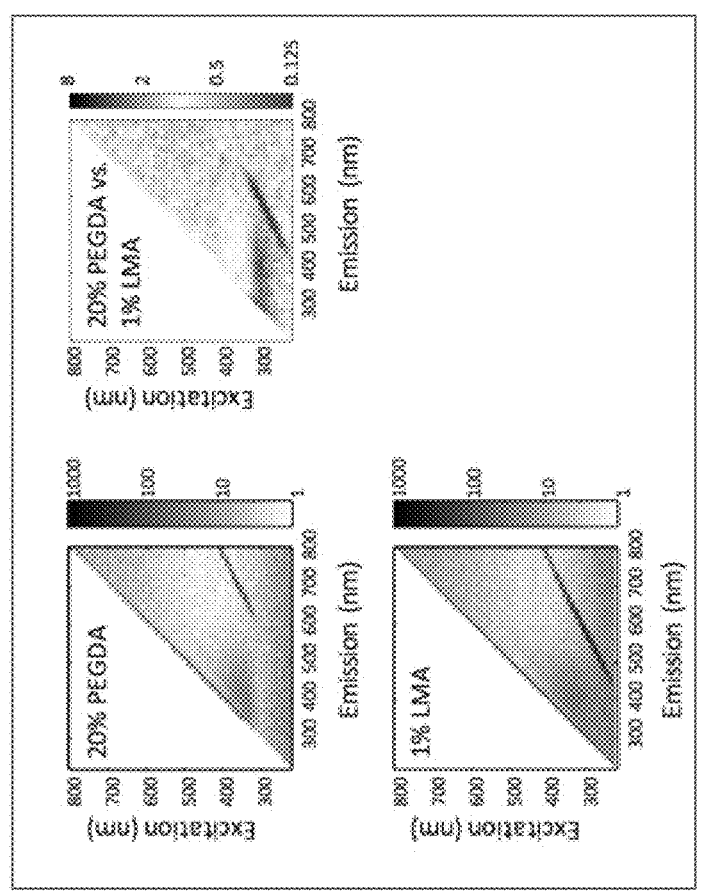
Figure 23E:
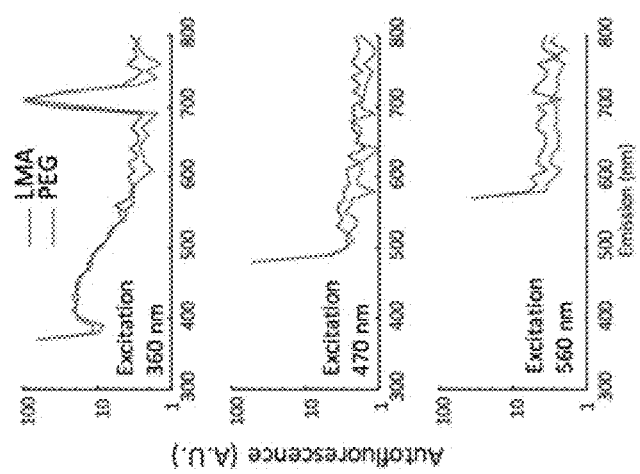

FIGS. 23A-23E compare the optical resolution and autofluorescence of different concentration PEG hydrogels and low-melt agarose. Optical resolution was determined by measuring point spread functions of embedded fluorescent nanobeads in 10%, 13.3% and 20% PEG hydrogels versus 1% low-melt agarose (LMA). FIG. 23A shows XY and XZ maximum projections of ~125-nm fluorescent beads. Scale bar (arrows), 1 µm. FIG. 23B shows relative intensity line scans along the center of fluorescent beads in each hydrogel in the x- and z-dimensions. FIG. 23C shows quantification of full width at half maximum (FWHM) of intensity profiles. FIGS. 23D-23E show comparison of autofluorescence of PEG hydrogel and agarose. Autofluorescence is slightly lower for PEG hydrogels. FIG. 23D shows excitation-emission matrix of relative fluorescence at wavelengths of 200-800 nm with a 10 nm and 5 nm slit width for 20% PEGDA (upper left), 1% low-melt agarose (lower left), and the ratio of autofluorescence of 20% PEGDA vs. 1% LMA. Red colors indicate lower autofluorescence of PEG. FIG. 23E shows emission spectra for excitation at common wavelengths for different fluorophores. Peak at twice the excitation wavelength is a measurement artifact.

All patents, patent applications, and published references cited herein are hereby incorporated by reference in their entirety. It should be emphasized that the above-described embodiments of the present disclosure are merely possible examples of implementations, merely set forth for a clear understanding of the principles of the disclosure. Many variations and modifications may be made to the above-described embodiment(s) without departing substantially from the spirit and principles of the disclosure. It can be appreciated that several of the above-disclosed and other features and functions, or alternatives thereof, may be desirably combined into many other different systems or applications. All such modifications and variations are intended to be included herein within the scope of this disclosure.

We claim:

1. A method for imaging a living organism in vivo, the method comprising:
    exposing at least one specimen to a hyper-osmotic solution to reduce a size of the at least one specimen, wherein the at least one specimen comprises one or more live whole organisms;
    placing the at least one specimen into a confined space within hydrogel on a substrate;
    photocrosslinking the hydrogel to immobilize without a use of a paralytic agent the at least one specimen within the confined space within the hydrogel such that the at least one specimen is kept alive and a movement of the at least one specimen within the hydrogel is restricted to 8 micrometres (µm) in the confined space; and
    imaging the at least one specimen.

2. The method of claim 1, further comprising delivering a stimulus to the at least one specimen and imaging a response of the at least one specimen to the stimulus.

3. The method of claim 1, wherein the at least one specimen is kept alive for at least 24 hours.

4. The method of claim 1, wherein imaging of the at least one specimen is done with light sheet microscopy.

5. The method of claim 4, wherein the at least one specimen is mounted using standard capillary mounting.

6. The method of claim 1, wherein the at least one specimen is mounted using glass slide mounting.

7. The method of claim 1, further comprising releasing the at least one specimen from the hydrogel such that the at least one specimen remains alive.

8. The method of claim 1, wherein imaging the at least one specimen includes image acquisition-based screening for detection of change in at least one of one or more fluorescent signals, movement of the at least one specimen, or quantities over time.

9. The method of claim 1, further comprising analysing an effect of one or more compounds introduced into the hydrogel on acquired signals related to the at least one specimen.

10. A method for immobilizing specimen in a multi-well plate comprising:
  exposing a population of specimens to a hyper-osmotic solution to reduce a size of the specimen of the population of specimens, wherein the specimens comprises one or more live whole organisms;
  mixing a curable hydrogel solution with the population of specimens;
  distributing mixture of the hydrogel solution and the specimens among a plurality of wells of a multi-well plate comprising multiple wells; and
  photocrosslinking the hydrogel solution to form hydrogel in each well to immobilize without a use of a paralytic agent the specimens in a confined space defined within the hydrogel, so that movement of the specimens being restricted to 8 micrometres (μm) in the confined space,
  wherein the specimens are maintained in a living state for a threshold amount of time.

11. The method of claim 10, further comprising delivering a stimulus to the specimens and imaging a response of the specimens to the stimulus.

12. The method of claim 10, wherein a threshold for maintaining the specimens in the living state is at least 24 hours.

13. The method of claim 10, further comprising settling the specimens on a bottom of the wells prior to photocrosslinking the hydrogel solution.

14. The method of claim 10, further comprising synchronizing the specimens prior to mixing the specimens and the hydrogel solution.

15. The method of claim 10, further comprising simultaneously delivering one or more stimuli to the specimens in different wells and imaging the specimens.

16. A method for preparing an organism for imaging, the method comprising:
  exposing at least one specimen to a hyper-osmotic solution to reduce a size of the at least one specimen, wherein the at least one specimen comprises one or more live whole organisms; and
  embedding the at least one specimen within a hydrogel in a confined space within the hydrogel by photocrosslinking the hydrogel to immobilize without a use of a paralytic agent the at least one specimen in the confined space within hydrogel, so that movement of the at least one specimen is restricted to 8 micrometres (μm) within the confined space and said specimen is maintained in a living state.

17. The method of claim 1, wherein the hydrogel comprises Polyethylene glycol (PEG) hydrogel and a photoinitiator.

18. The method of claim 1, further comprising cooling the at least one specimen prior to photocrosslinking the hydrogel.

19. The method of claim 1 further comprising:
  creating in the hydrogel one or more microchannels, the one or more microchannels being in communication with the confined space to deliver one or more chemical agents to the at least one specimen;
  introducing the one or more chemical agents into the one or more microchannels; and
  observing a biological response or neural response of the at least one specimen to the one or more chemical agents.

* * * * *